United States Patent [19]

Mookherjee et al.

[11] 4,446,125

[45] May 1, 1984

[54] USE OF ISOMERIC FARNESENE PRODUCT-BY-PROCESS FOR AUGMENTING OR ENHANCING THE AROMA OR TASTE OF FOODSTUFFS, CHEWING GUMS, MEDICINAL PRODUCTS AND TOOTHPASTES

[75] Inventors: Braja D. Mookherjee, Holmdel; Robert W. Trenkle, Bricktown, both of N.J.; Bernard J. Chant, Rye, N.Y.; Anton V. Ouwerkerk, Livingston, N.J.; Venkatesh Kamath, Red Bank, N.J.; Cynthia J. Mussinan, Bricktown, N.J.

[73] Assignee: International Flavors & Fragrances Inc., New York, N.Y.

[21] Appl. No.: 461,476

[22] Filed: Jan. 27, 1983

Related U.S. Application Data

[63] Continuation-in-part of Ser. No. 292,392, Aug. 13, 1981, Pat. No. 4,376,068.

[51] Int. Cl.³ ............................................. A23L 1/226

[52] U.S. Cl. ...................................... 424/49; 424/358; 426/3; 426/534; 426/538; 131/276

[58] Field of Search ........................... 426/3, 534, 538; 424/49, 358

[56] References Cited

U.S. PATENT DOCUMENTS 4,376,068  3/1983  Mookherjee et al. ........... 252/522 R

*Primary Examiner*—Joseph M. Golian
*Attorney, Agent, or Firm*—Arthur L. Liberman

[57] ABSTRACT

Described are isomeric mixtures of farnesene prepared by dehydrating nerolidol using potassium bisulfate or paratoluene sulfonic acid and then distilling the resultant product at particular temperature ranges and particular pressure ranges in order to prepare a composition of matter useful for augmenting or enhancing the fresh green, herbaceous aroma and taste nuances of foodstuffs, chewing gums, medicinal products and toothpastes.

7 Claims, 32 Drawing Figures

GLC PROFILE FOR EXAMPLE I (NEROLIDOL REACTANT)
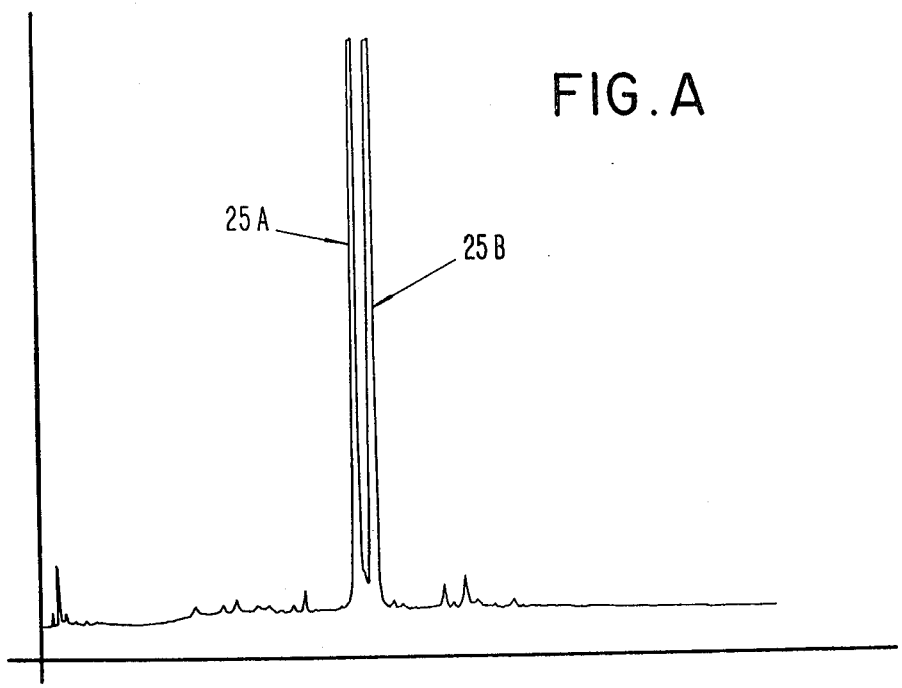
FIG. A
GLC PROFILE FOR EXAMPLE III (NEROLIDOL REACTANT)
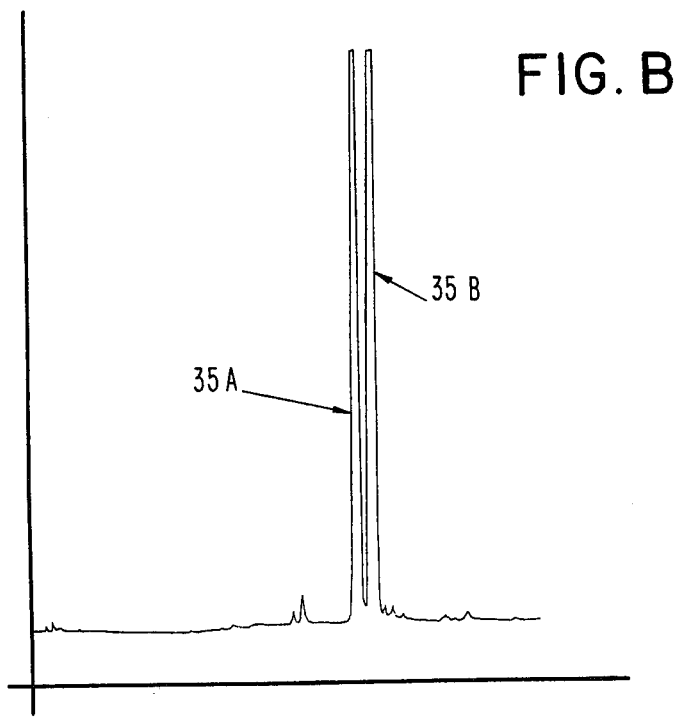
FIG. B

GLC PROFILE FOR EXAMPLE I

GLC PROFILE FOR EXAMPLE I.

IR SPECTRUM FOR EXAMPLE I, BULKED FRACTIONS 4-18.

IR SPECTRUM FOR PEAK II OF FIG.2 OF EXAMPLE I.

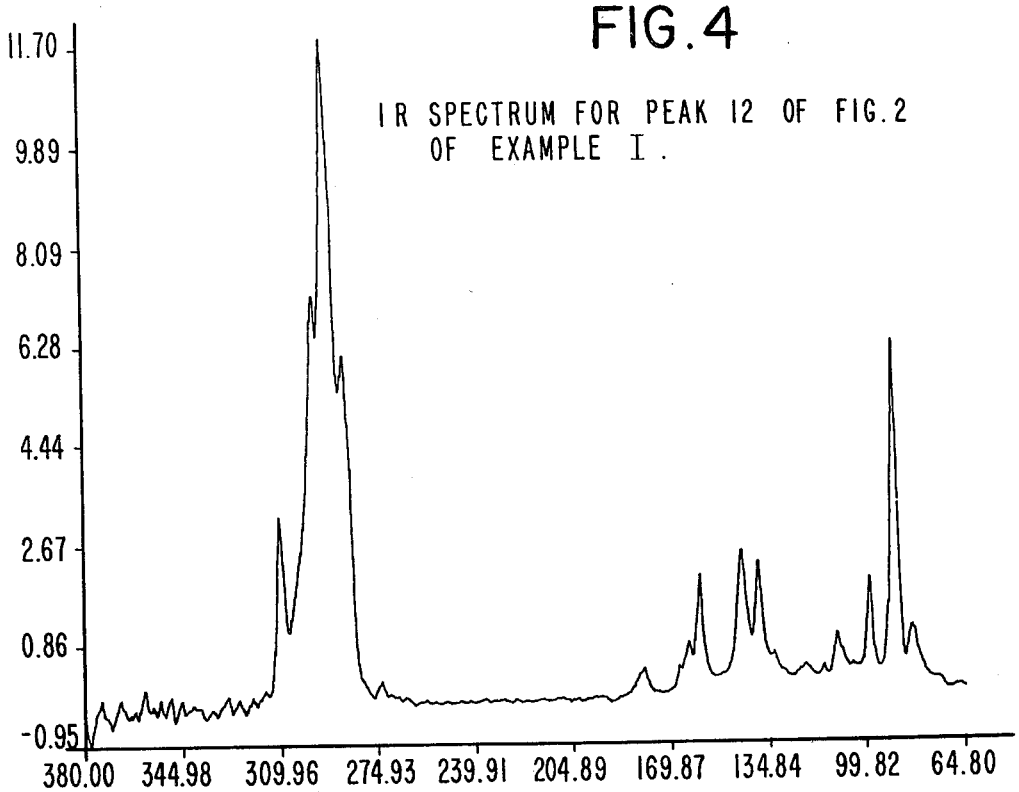
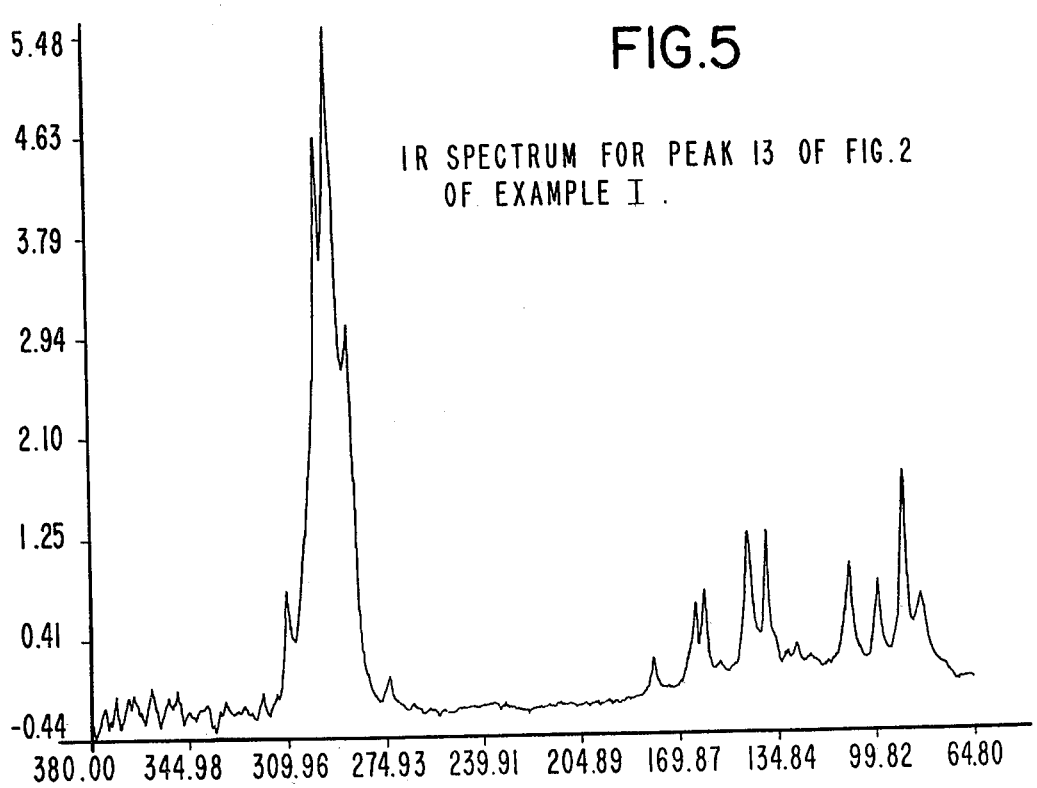

IR SPECTRUM FOR PEAK 14 OF FIG. 2 OF EXAMPLE I.

NMR SPECTRUM FOR PEAK 11 OF FIG. 2 OF EXAMPLE I.

NMR SPECTRUM FOR PEAK 12 OF FIG.2 OF EXAMPLE I.

NMR SPECTRUM FOR PEAK 13 OF FIG.2 OF EXAMPLE I.

NMR SPECTRUM FOR PEAK 14 OF FIG.2 OF EXAMPLE I.

GLC PROFILE FOR EXAMPLE II.

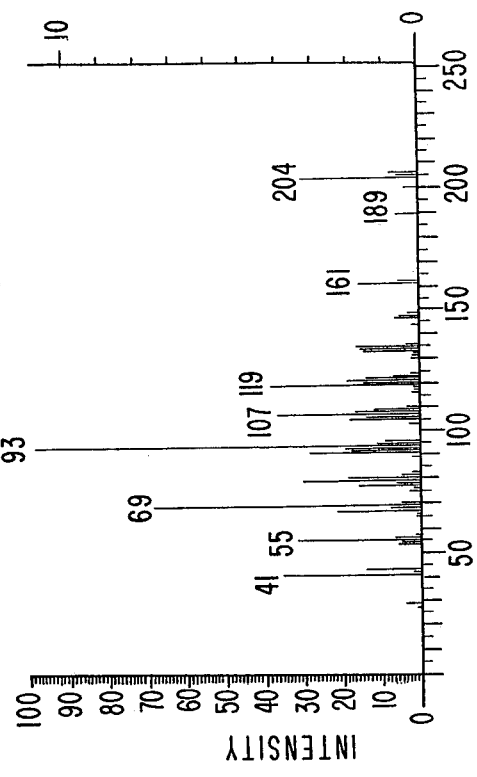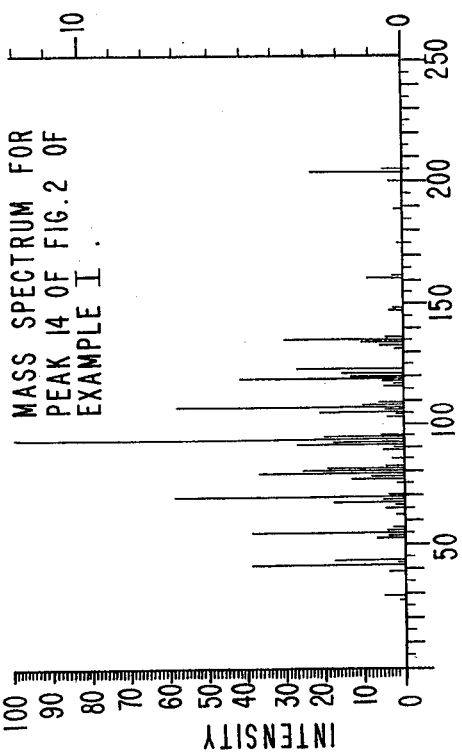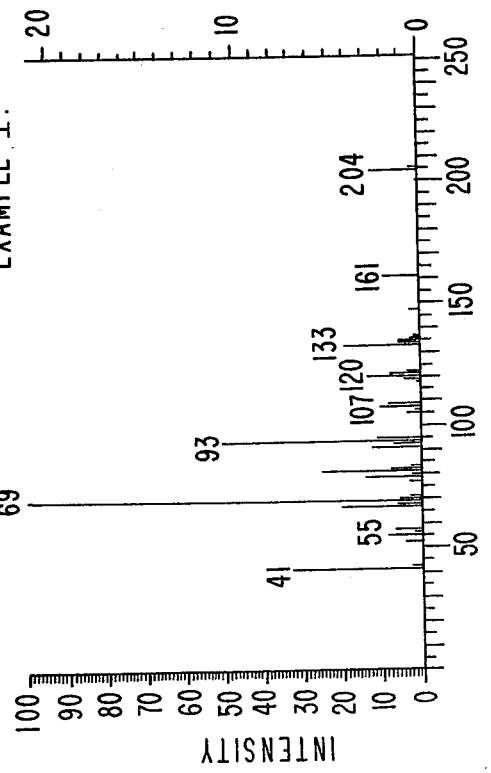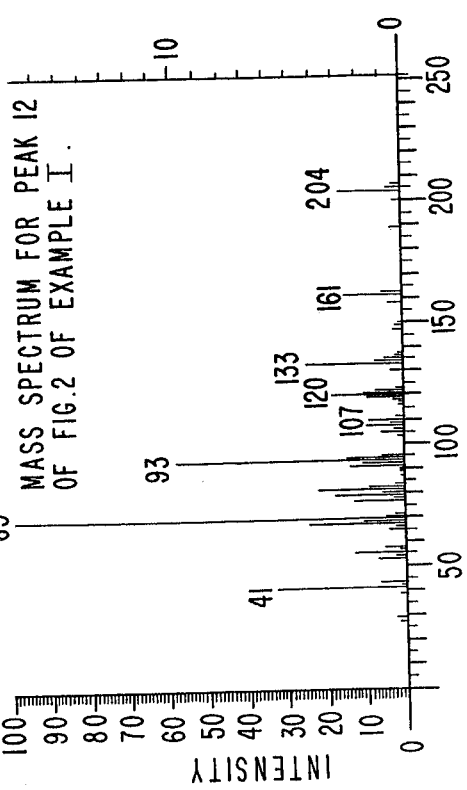

GLC PROFILE FOR EXAMPLE III — CRUDE.

GLC PROFILE FOR FRACTION 1 OF EXAMPLE III.

GLC PROFILE FOR FRACTION 2 OF EXAMPLE III.

GLC PROFILE FOR FRACTION 3 OF EXAMPLE III.

GLC PROFILE FOR FRACTION 4 OF EXAMPLE III.

GLC PROFILE FOR FRACTION 5 OF EXAMPLE III.

GLC PROFILE FOR FRACTION 6 OF EXAMPLE III.

GLC PROFILE FOR FRACTION 7 OF EXAMPLE III.

GLC PROFILE FOR FRACTION 8 OF EXAMPLE III.

GLC PROFILE FOR FRACTION 9 OF EXAMPLE III.

GLC PROFILE FOR BULKED FRACTIONS 4-7 OF EXAMPLE III.

IR SPECTRUM FOR BULKED FRACTIONS 4-7 OF EXAMPLE III.

GLC PROFILE FOR EXAMPLE IV.
(BULKED FRACTIONS 4-8)

GLC PROFILE FOR EXAMPLE IV.
(CRUDE REACTION PRODUCT)

USE OF ISOMERIC FARNESENE PRODUCT-BY-PROCESS FOR AUGMENTING OR ENHANCING THE AROMA OR TASTE OF FOODSTUFFS, CHEWING GUMS, MEDICINAL PRODUCTS AND TOOTHPASTES

This application is a continuation-in-part of application for United States Letters Patent, Ser. No. 292,392 filed on Aug. 13, 1981 and now U.S. Pat. No. 4,376,068.

BACKGROUND OF THE INVENTION

The present invention relates to farnesene isomer mixtures containing, but not limited to, compounds defined according to the structures:

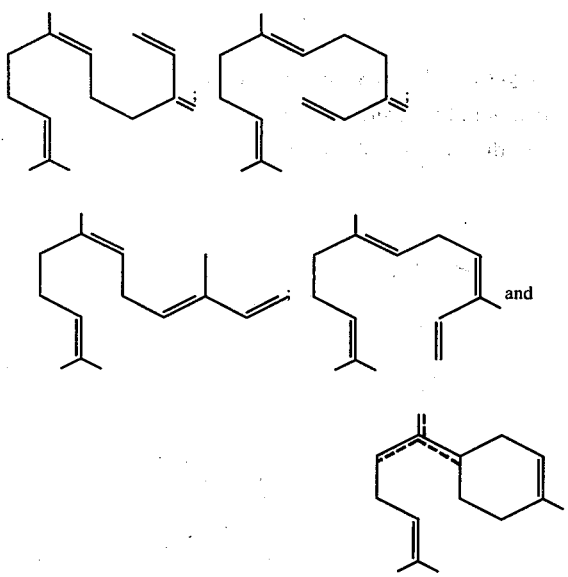

and uses of such mixtures in augmenting or enhancing the aroma or taste of foodstuffs, chewing gums, medicinal products and toothpastes.

The compositions of our invention are prepared by dehydrating nerolidol compositions of matter containing their nerolidol isomers:

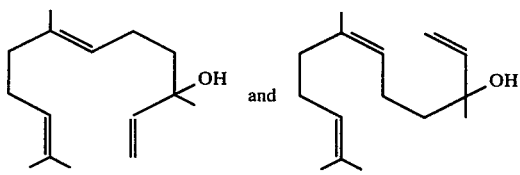

using potassium bisulfate or paratoluene sulfonic acid dehydrating agents.

There has been considerable work performed relating to substances which can be used to augment or enhance flavors of foodstuffs, chewing gums, medicinal products and toothpastes. The substances are used to diminish the use of natural materials, some of which may be in short supply and to provide more uniform properties in the finished product.

There has been considerable work performed relating to substances which can be used to augment or enhance flavors of foodstuffs. The substances are used to diminish the use of natural materials, some of which may be in short supply and to provide more uniform properties in the finished product.

Fresh green, herbaceous aroma and taste nuances are particularly desirable in several types of foodstuffs, e.g., citrus beverages, orange flavored ice creams and the like.

Arctander "Perfume and Flavor Chemicals (Aroma Chemicals)" at monograph 1378 discloses "Farnesal", 2,6,10-trimethyl-2,6,10-dodecatrien-12-al to have a very mild, sweet oily, slightly woody, tenacious odor. On the other hand, Arctander also describes, at Monograph 1379, Farnesene, 2,6,10-trimethyl-2,6,9,11-dodecatetraene defined according to the structure:

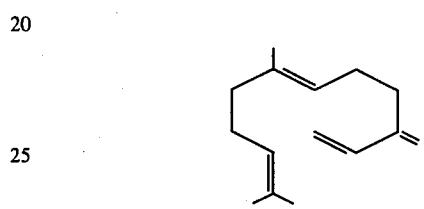

to have a very mild, sweet and warm, rather nondescript odor of good tenacity. Arctander further states that apart from some possible use in the reconstruction of certain essential oils, there is to the author's knowledge, very little, if any, use for this sesquiterpene in perfumery as such. Arctander further states that Farnesene having the structure:

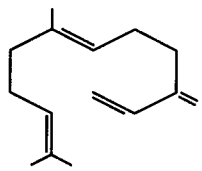

is produced by dehydration of Farnesol by heat with a potassium dehydrating agent or from Nerolidol by heat with acetic anhydride.

Brieger, et al, J. Org. Chem. Volume 34, Number 12, December 1969, in their paper "The Synthesis of trans,-trans-α-Farnesene" discloses dehydration of nerolidol using bisulfate at 170° C. to yield a number of Farnesene isomers according to the reaction:

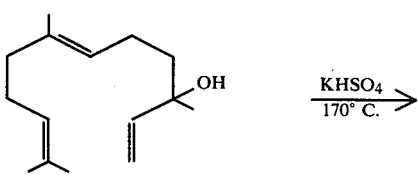

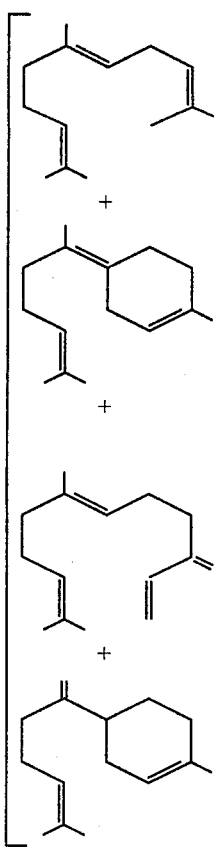

Brieger, et al also discloses the dehydration of Farnesol using potassium bisulfate at 170° C. as follows:

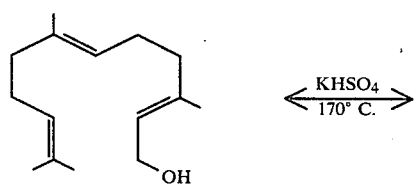

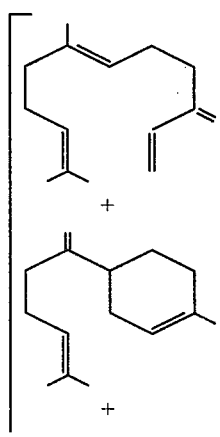

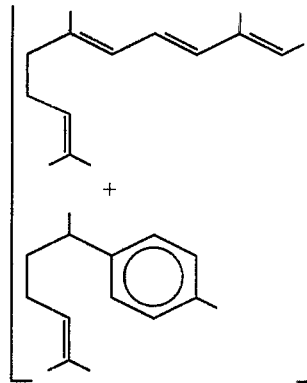

Brieger also teaches the dehydration of Farnesol using potassium hydroxide at 210° C. to yield certain isomers according to the following reaction:

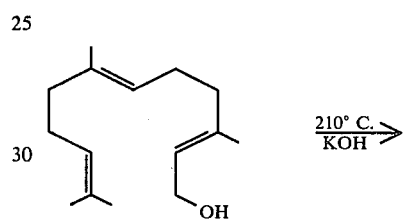

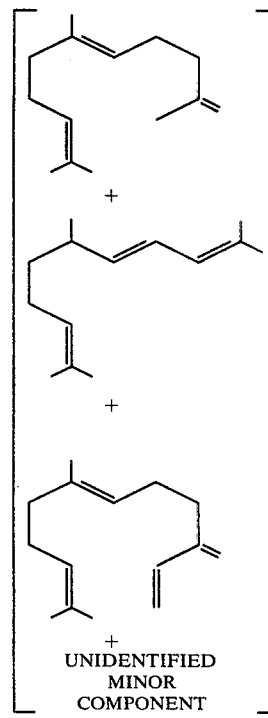

Anet, Aust. J. Chem., 1970, 23, 2101-8, in a paper entitled "Synethesis of (E,Z)-α-, (Z,Z)-α-, and (Z)-β-Farnesene" discloses the dehydration of (E)-nerolidol having the structure:

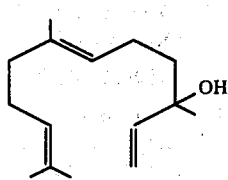

in the presence of such dehydrating agents as phosphoryl chloride in pyridene to yield the compounds having the structures:

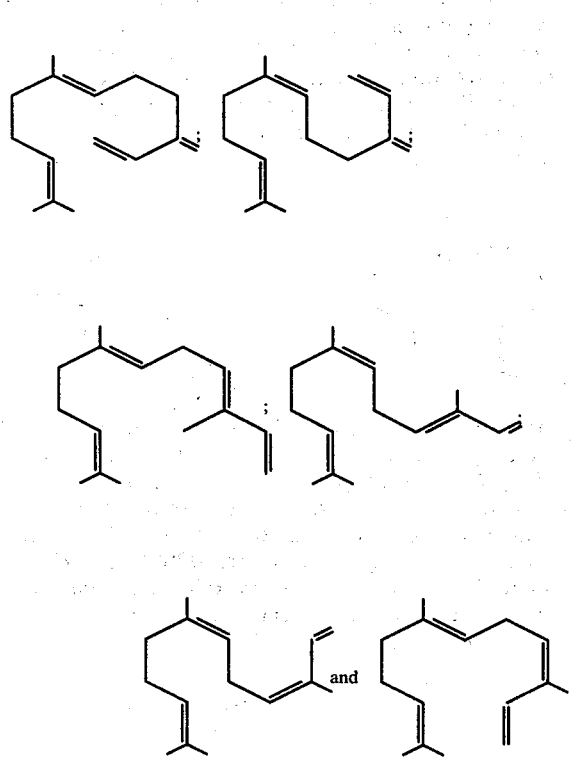

according to the reaction:

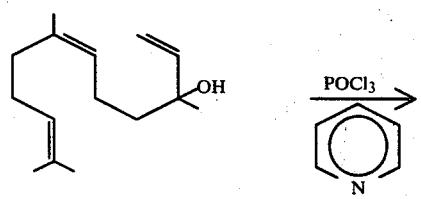

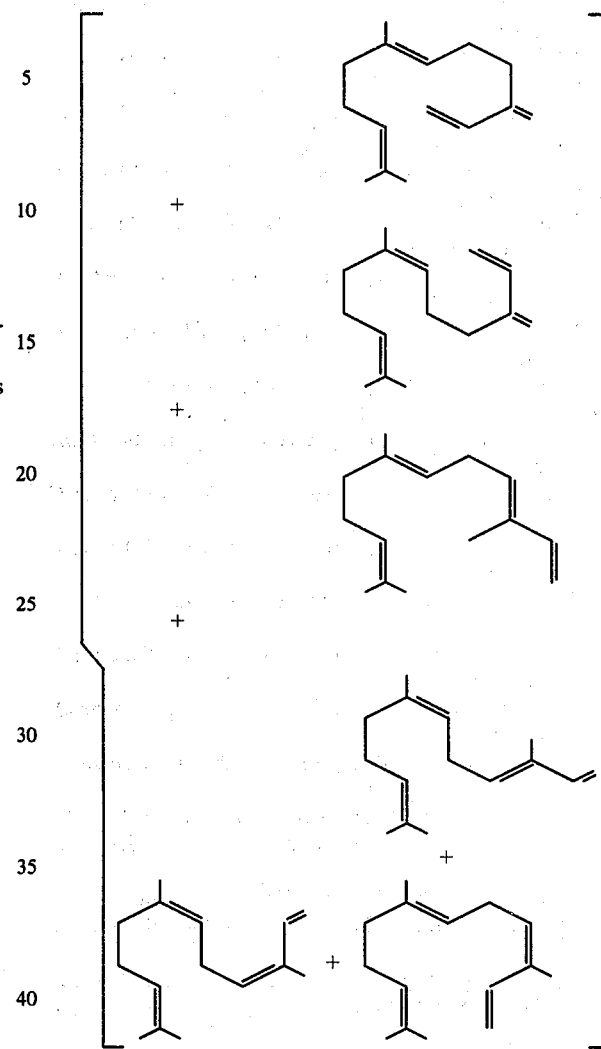

In a paper by Hattori, et al entitled "Chemical Composition of the Absolute from Gardenia Flower" and in another paper by Tsuneya, et al entitled "GC-MS Analysis of Gardenia Flower Volatiles", it is disclosed that α-farnesene is existent in gardenia flower absolute. The Hattori, et al and Tsuneya, et al papers are published in the "VII International Congress of Essential Oils"; Japan Flavor and Fragrance Manufacturers' Association, Tokyo (1979) at pages 451 and 454, respectively (papers 128 and 129, respectively).

Nothing in the prior art cited above indicates the subject matter of our invention.

BRIEF DESCRIPTION OF THE DRAWINGS

FIG. A is the GLC profile for the nerolidol used as a reactant in Example I.

FIG. B is the GLC profile for the nerolidol used as a reactant in Example III.

FIG. 4 is the infra-red spectrum for peak 12 of the GLC profile of FIG. 2.

FIG. 5 is the infra-red spectrum of peak 13 of the GLC profile of FIG. 2.

FIG. 11 is the mass spectrum for peak 11 of the GLC profile of FIG. 2.

FIG. 12 is the mass spectrum for peak 12 of the GLC profile of FIG. 2.

FIG. 13 is the mass spectrum for peak 13 of the GLC profile of FIG. 2.

FIG. 14 is the mass spectrum for peak 14 of the GLC profile of FIG. 2.

DETAILED DESCRIPTION OF THE DRAWINGS

Figure 1:
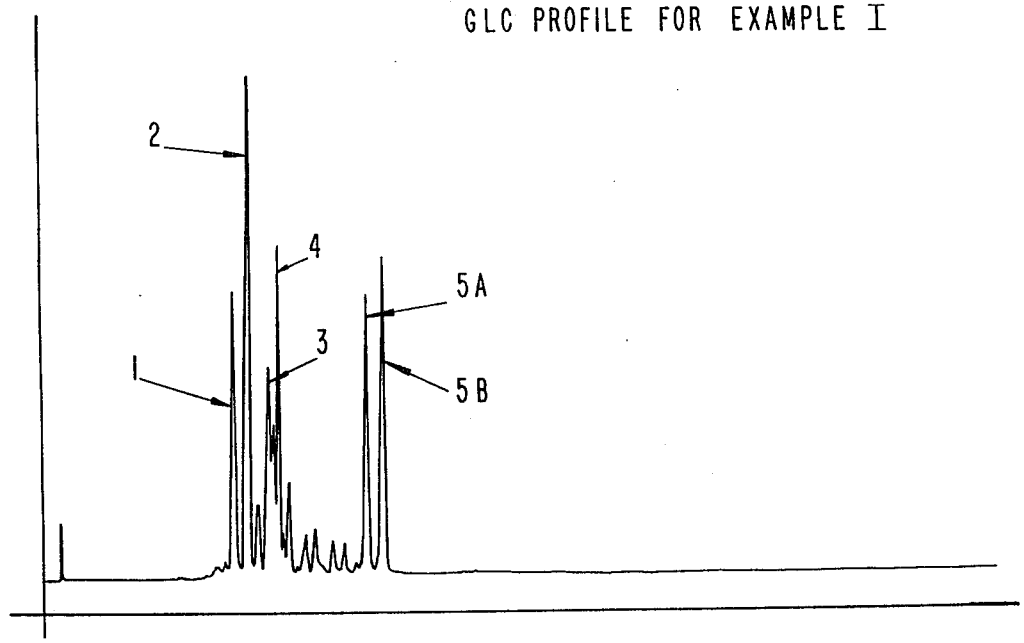
FIG. 1 is the GLC profile subsequent to basic wash but prior to distillation for the reaction product of Example I.

A. DETAILED DESCRIPTION OF FIG. A.

FIG. A is the GLC profile for the nerolidol reactant used for Example I. Reference numeral 25A and reference numeral 25B indicate the nerolidol reactant peaks for the compounds having the structures:

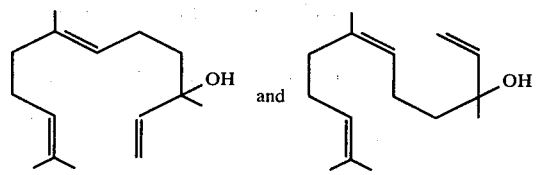

The GLC conditions are: 5% Carbowax 10'×⅛" column programmed at 100°-230° C. at 4° C. per minute.

FIG. B is the GLC profile for the nerolidol reactant used in Example III. Reference numeral 35A and 35B indicate the peaks for the nerolidol reactant on this GLC profile. The nerolidol reactants have the structures:

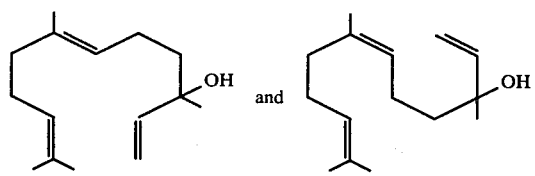

The GLC conditions are: 10'×⅛" 5% Carbowax column programmed at 100°-230° C. at 4° C. per minute.

FIG. 1 is the GLC profile for the reaction product of Example I subsequent to the base wash but prior to distillation. The GLC conditions are: 10'×⅛" 5% Carbowax column programmed at 100°-220° C. at 4° C. per minute. The peak indicated by reference numeral 1 indicates the compound having the structure:

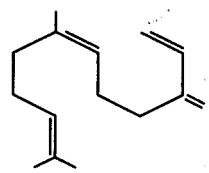

The peak indicated by reference numeral 2 is for the compound having the structure:

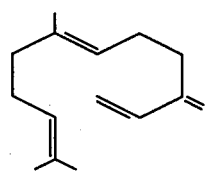

The peak indicated by reference numeral 3 is for the compound having the structure:

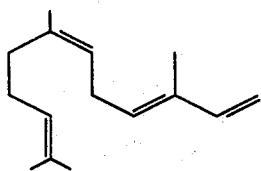

The peak indicated by reference numeral 4 is for the compounds having the structures:

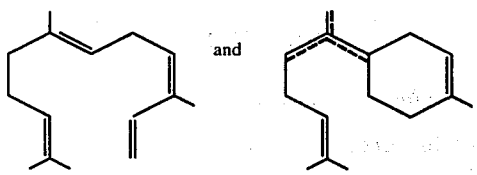

wherein the structure:

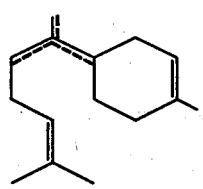

represents a mixture of compounds wherein in each of the molecules of the mixture, one of the dashed lines represents a pi double bond and each of the other of the dashed lines are indicative of single bonds. The peaks indicated by reference numerals 5A and 5B are isomers of nerolidol, the starting material, said nerolidol having the structures:

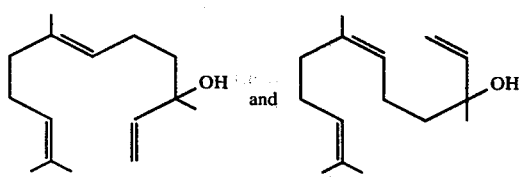

Figure 2:
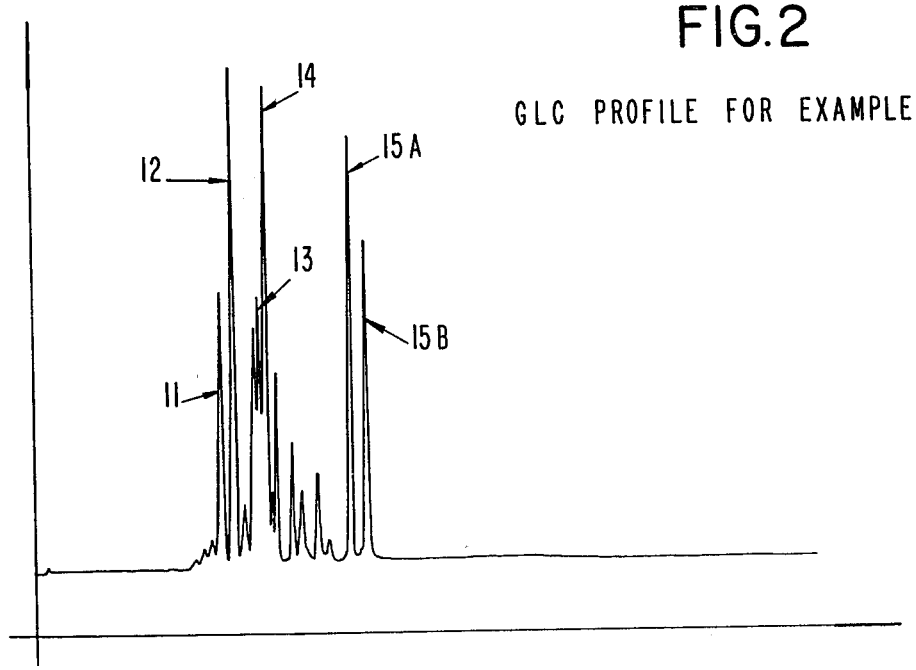
FIG. 2 is the GLC profile for bulked fractions 4-18 of the distillation product of the reaction product of Example I.
Figure 2A:
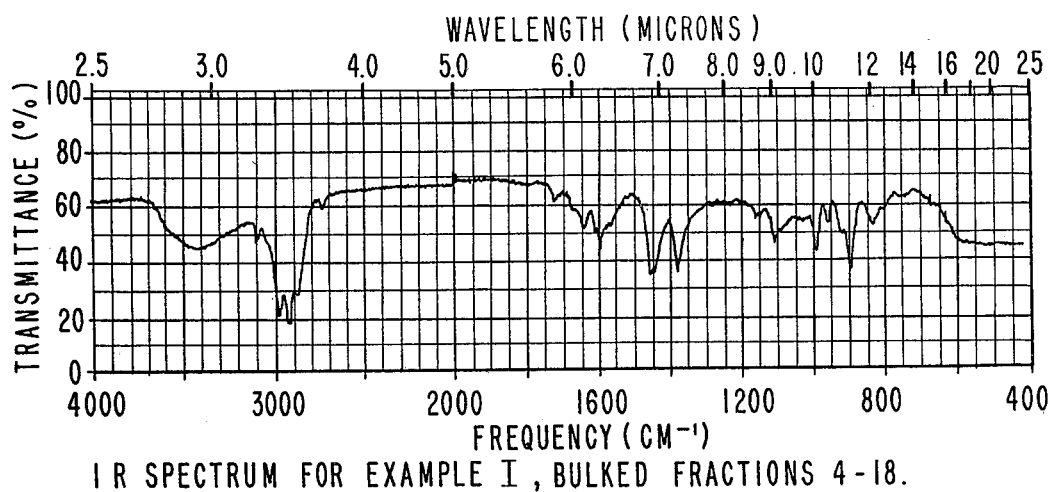
FIG. 2(A) is the infra-red spectrum for bulked fractions 4-18 of the distillation product of the reaction product of Example I.
Figure 3:
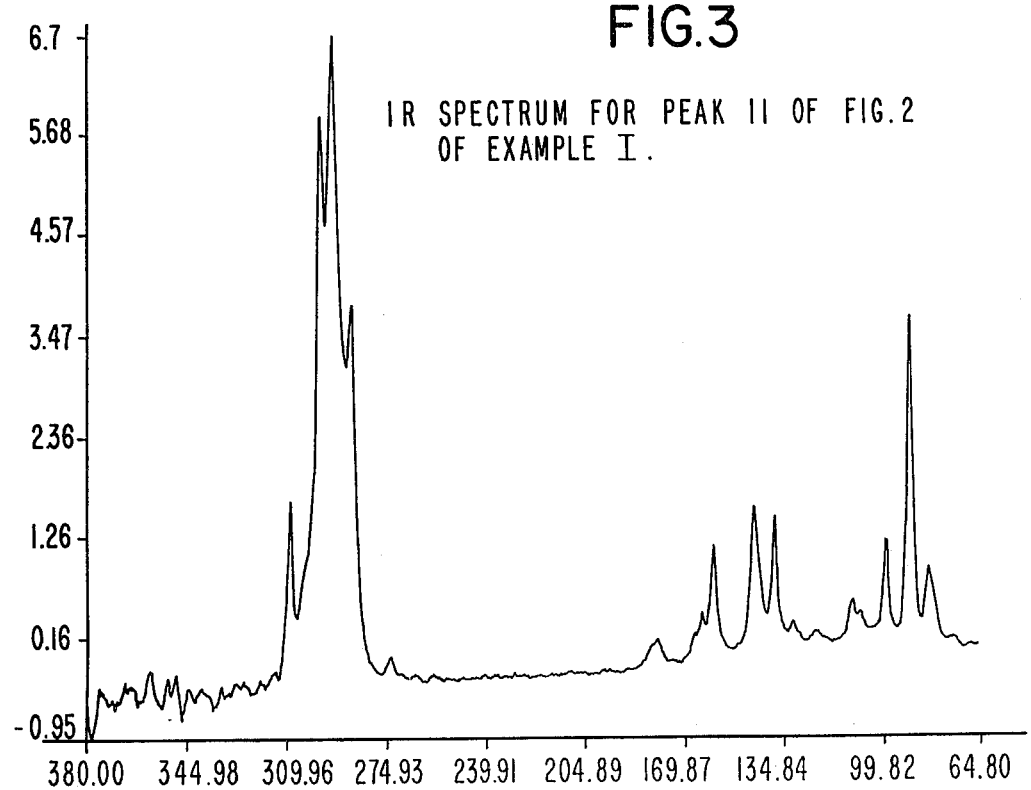
FIG. 3 is the infra-red spectrum for peak 11 of the GLC profile of FIG. 2.
Figure 6:
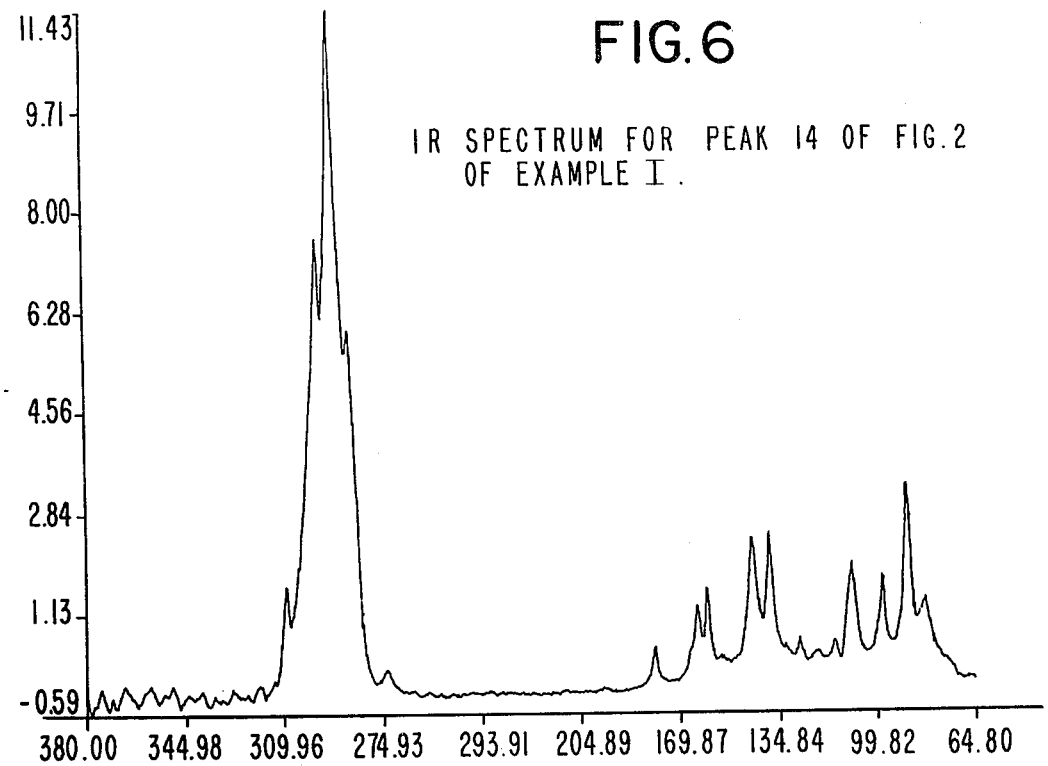
FIG. 6 is the infra-red spectrum for peak 14 of the GLC profile of FIG. 2.
Figure 7:
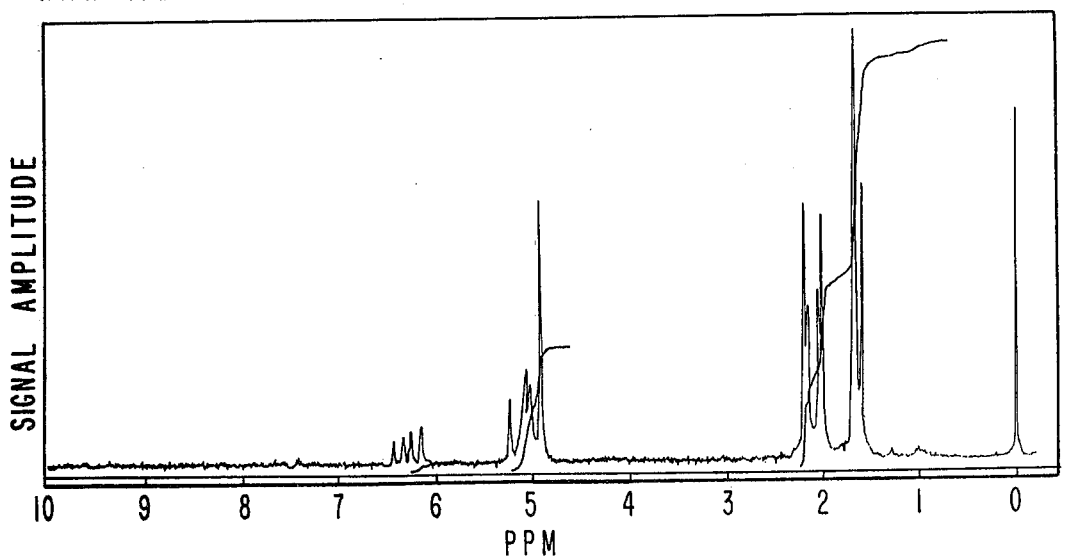
FIG. 7 is the NMR spectrum for peak 11 of the GLC profile of FIG. 2.
Figure 8:
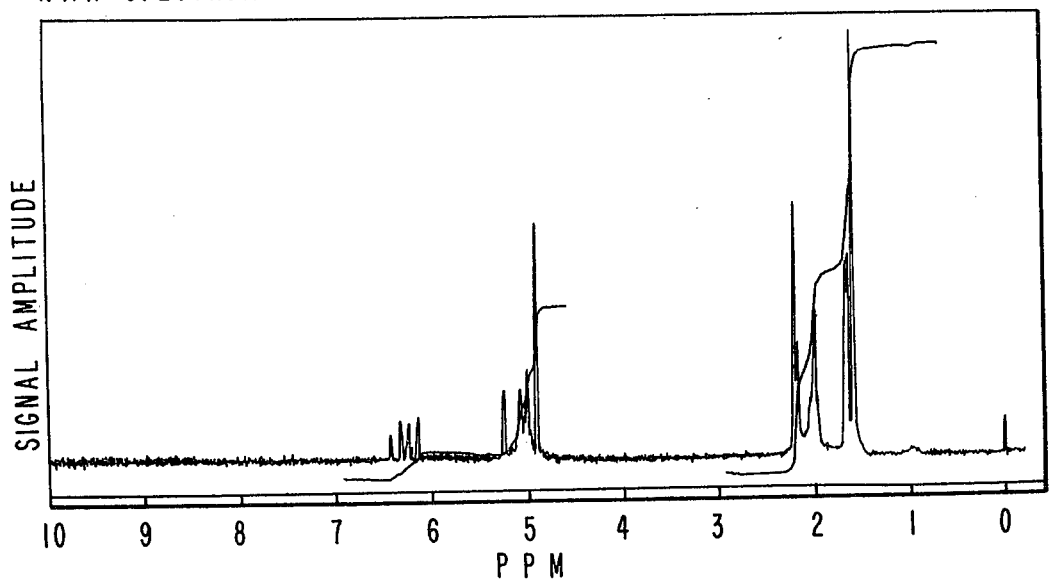
FIG. 8 is the NMR spectrum for peak 12 of the GLC profile of FIG. 2.
Figure 9:
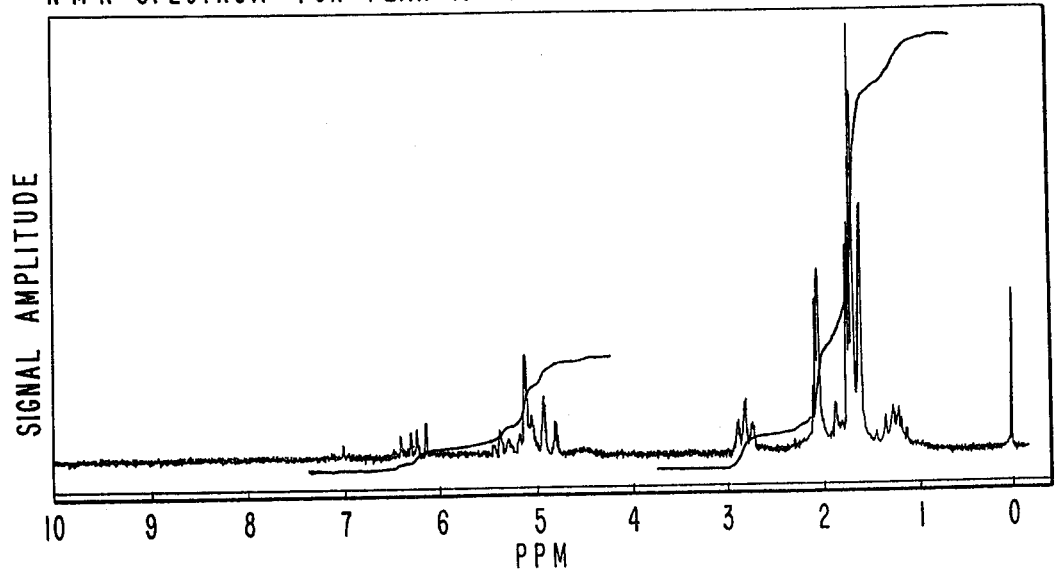
FIG. 9 is the NMR spectrum for peak 13 of the GLC profile of FIG. 2.
Figure 10:
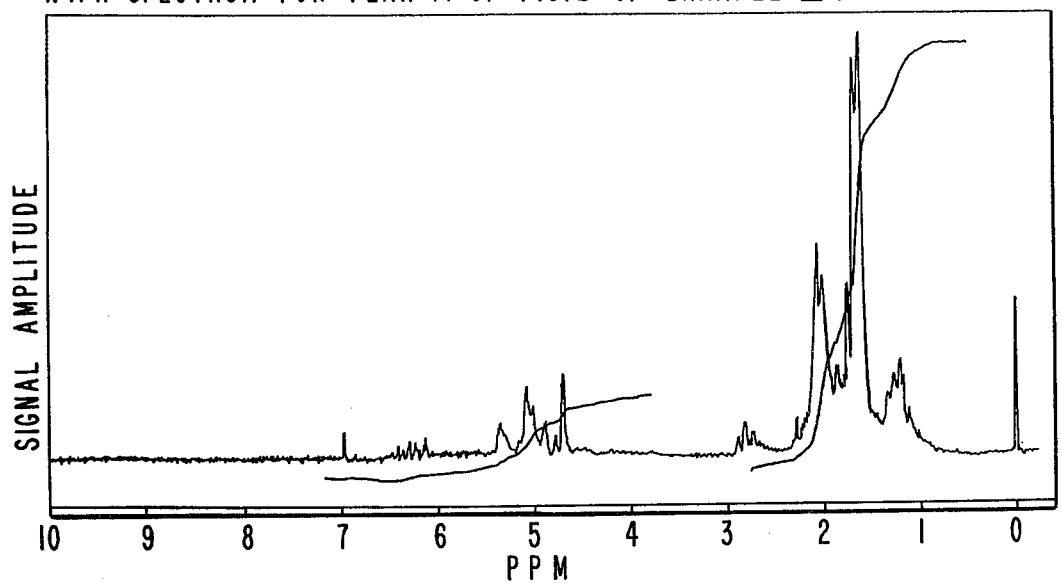
FIG. 10 is the NMR spectrum for peak 14 of the GLC profile of FIG. 2.

FIG. 2 is the GLC profile for bulked fractions 4–18 of the distillation product of the reaction product of Example I containing isomers of farnesene and isomers of nerolidol. Conditions: 10′×⅛″ 5% Carbowax column programmed at 100°–220° C. at 4° C. per minute. The peak indicated by reference numeral 11 is for the compound having the structure:

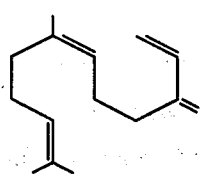

The peak indicated by reference numeral 12 is for the compound having the structure:

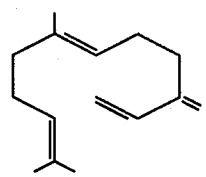

The peak indicated by reference numeral 13 is for the compound having the structure:

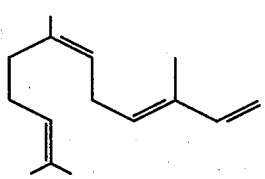

The peak indicated by reference numeral 14 is the for compounds defined according to the structures:

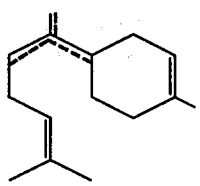

wherein the structure:

is indicative of a mixture wherein in each of the molecules of the mixture, one of the dashed lines represents a pi double bond and each of the other of the dashed lines is indicative of a single bond. The peaks indicated by reference numeral 15A and 15B are for isomers of nerolidol having the structures:

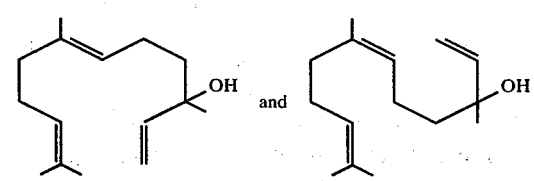

Figure 15:
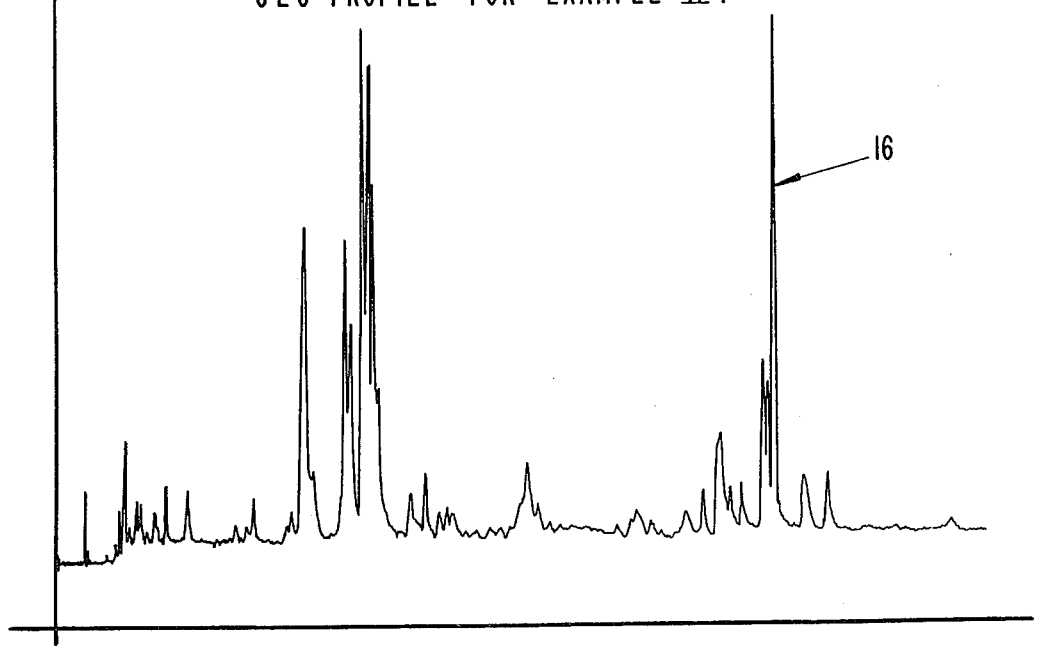
FIG. 15 is the GLC profile for the magnolia headspace of Example II.

FIG. 15 is the GLC profile for the magnolia headspace produced according to Example II. The peak indicated by reference 16 is for α-farnesene which contains compounds having the structures:

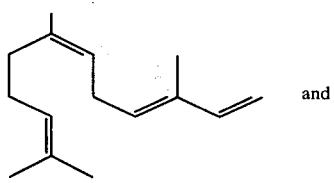

and

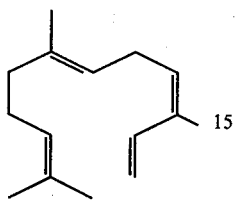

among other compounds. The conditions for this GLC profile are: SF 96 column, isothermal, 190° C.

Figure 18:
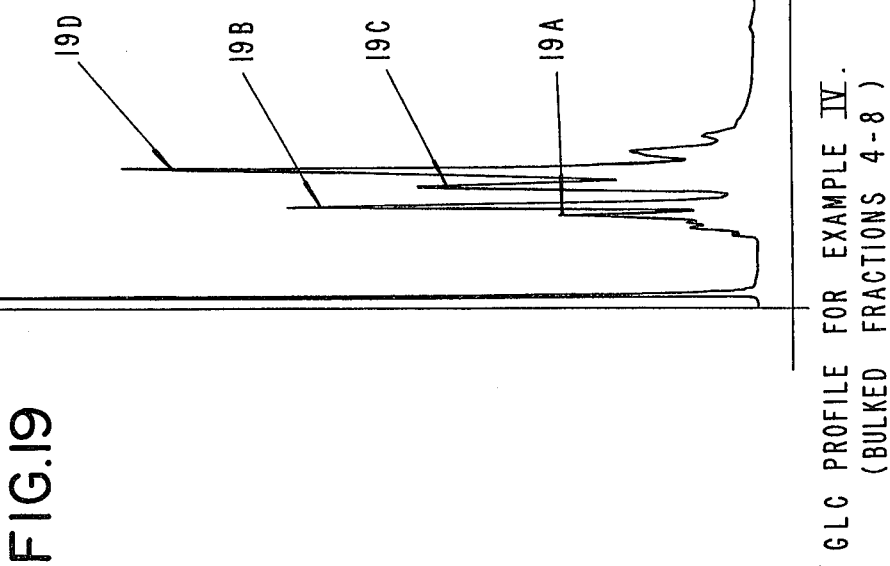
FIG. 18 is the GLC profile for the crude reaction product of Example IV.

FIG. 18 is the GLC profile for the crude reaction product of Example IV. The conditions for this GLC profile are: 10'×⅛" 5% Carbowax column programmed at 220° C. isothermal. The peaks indicated by reference numerals 17A and 17B are for various farnesene isomers containing, interalia, the compound having the structure:

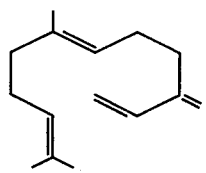

The peaks indicated by reference numerals 18A, 18B and 18C are for farnesyl acetate isomers having the structures:

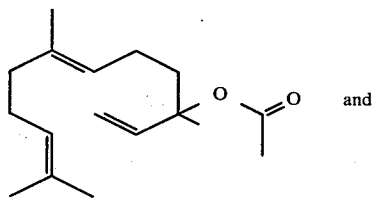

and

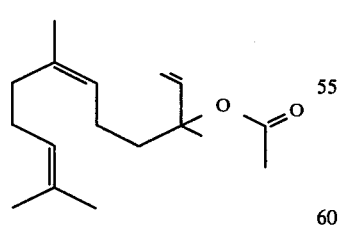

Figure 19:
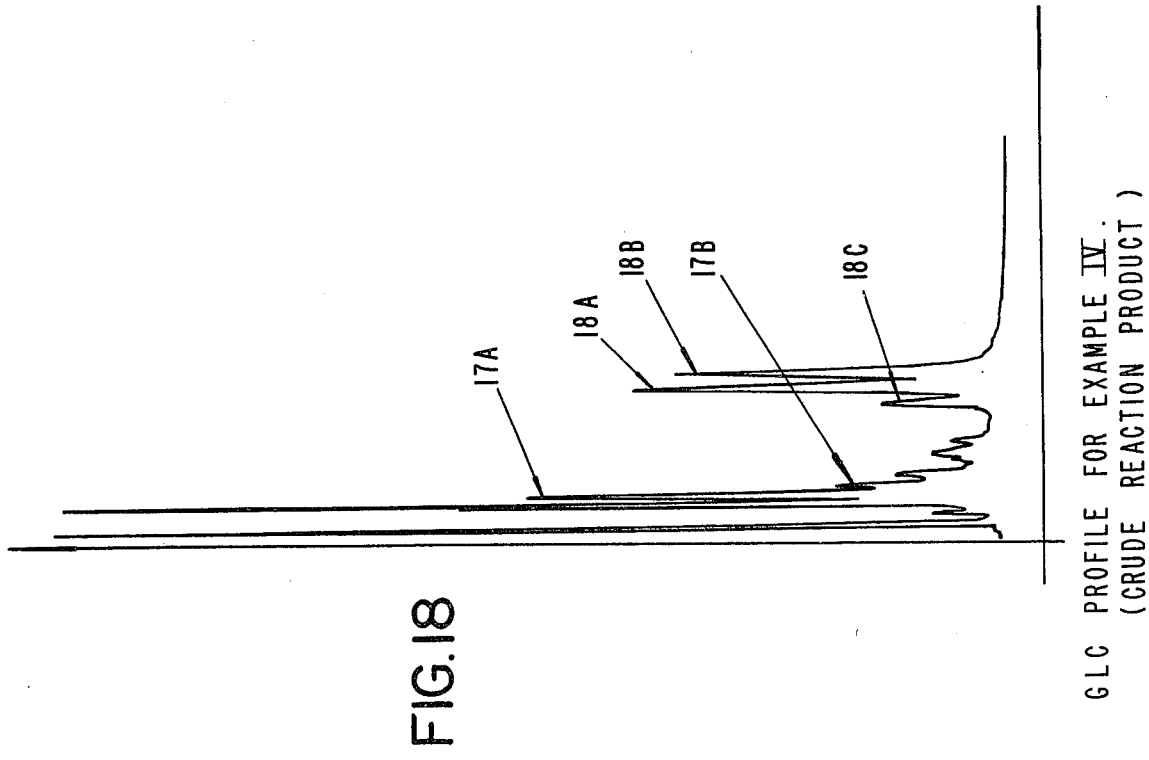
FIG. 19 is the GLC profile for bulked fractions 4-8 of the distillation product of the reaction product of Example IV.

FIG. 19 is the GLC profile for bulked fractions 4–8 of the distillation product of the reaction product of Example IV. The conditions for this GLC profile are: 10'×⅛" 5% Carbowax column programmed at 200° C. isothermal. The peaks indicated by reference numeral 19A, 19B, 19C and 19D are for farnesene isomers containing the compound having the structure:

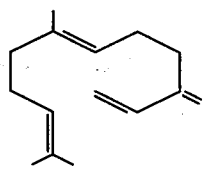

as well as other compounds.

THE INVENTION

It has now been discovered that novel solid and liquid foodstuffs, chewing gums, medicinal products and toothpastes having fresh green, herbaceous aromas may be provided by the use of an isomeric mixture of farnesene derivatives (containing a number of other compounds) defined according to the process for producing same by the dehydration of various isomeric mixtures of E(trans) and Z(cis) nerolidol having the structures:

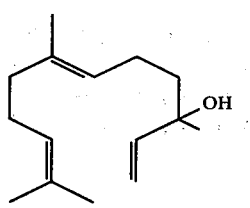

(E or trans) and

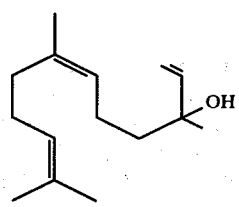

(Z or cis)

using a potassium acid sulfate or paratoluene sulfonic acid dehydration catalyst over a particular temperature and pressure range for a given reaction time range.

The reaction to produce the products of our invention may be set forth as follows:

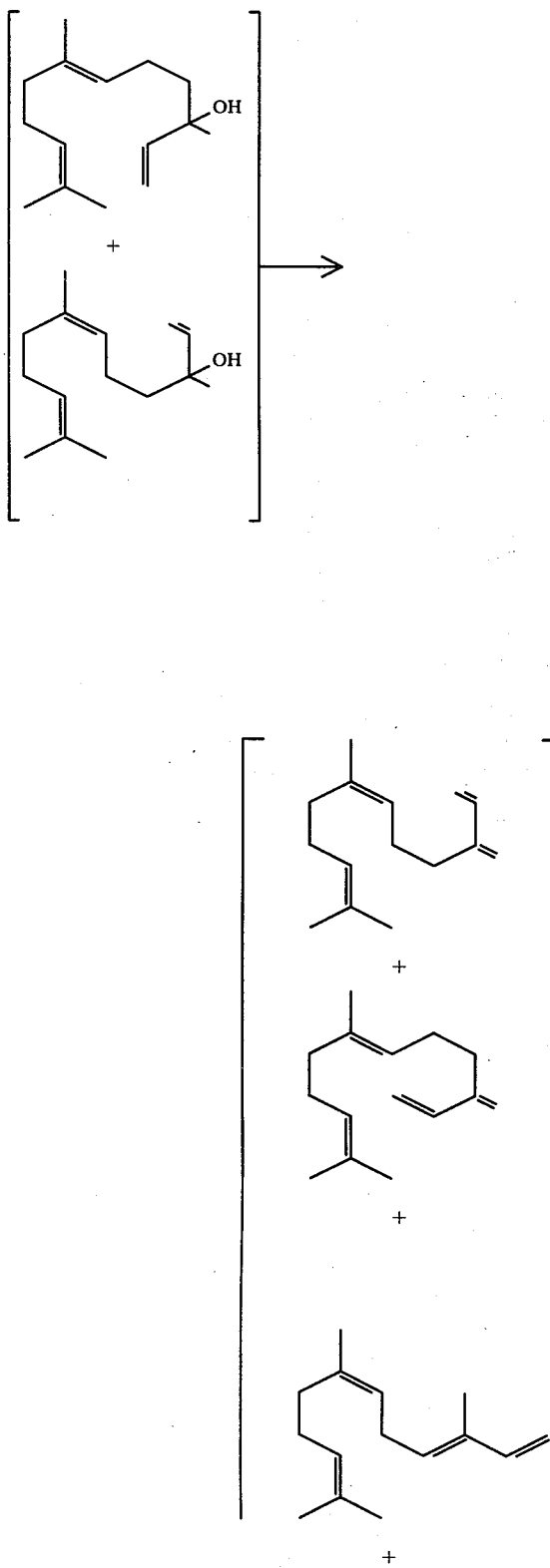

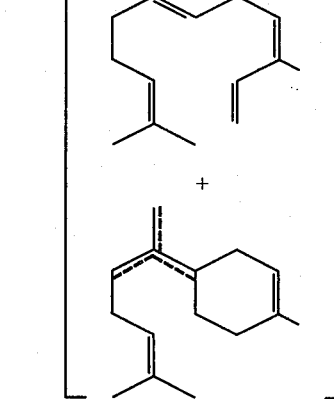

wherein the catalyst used may be potassium acid sulfate (KHSO₄) or paratoluene sulfonic acid.

The ratio of E(trans) or Z(cis) nerolidol isomers having the structures:

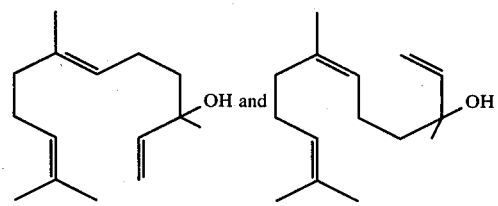

used in the reaction mass may vary from 25:100 E isomer:Z isomer up to 100:25 E isomer:Z isomer. Although the isomer mixture is substantially the same whether using the paratoluene sulfonic acid catalyst or the potassium acid sulfate catalyst, the specific reaction conditions using the two catalysts are different.

Thus, when using a potassium acid sulfate catalyst, the temperature range is preferably between 180° and 200° C. and it is necessary to utilize a solvent for the reaction mass which will:

(a) be inert to the reaction;
(b) have a boiling point at the reaction pressure which will be conveniently greater than the reaction temperature so that the solvent will not volatilize from the reaction mass.

Thus, when using a potassium acid sulfate catalyst at a temperature in the range of 180°–200° C., it is most preferable to use a heavy hydrocarbon mineral oil, for example, Primol ® (manufactured by the Exxon Corporation of Linden, New Jersey). Other inert solvents such as toluene and xylene may be used but, when using toluene, the pressure over the reaction mass must be such that the reaction mass will reflux in the range of 180°–200° C. Thus, when using a toluene or xylene solvent, a positive nitrogen pressure over the reaction mass is necessary in order to maintain the reaction temperature at 180°–200° C. Thus, when using a potassium acid sulfate catalyst, not only is the temperature range important, e.g. 180°–200° C., but the pressure range is equally as important; from 1 up to 200 atmospheres pressure. Using pressures greater than 1 atmosphere necessitates the use of high pressure equipment and appropriate safety proportions.

Whether using a potassium acid sulfate catalyst or a paratoluene sulfonic acid catalyst, it is necessary to remove the water of reaction as it is formed. Thus, during refluxing, a phase separation column is necessarily utilized whereby the water of reaction is removed during the course of the reaction. For example, a Bidwell water trap is the type of trap used in the laboratory when removing the water of reaction.

Accordingly, the time of reaction is necessarily dictated by the rate at which the nerolidol reaction mixture is added to the catalyst/solvent mixture. It is preferable to add the nerolidol to the catalyst/solvent mixture over a period of between 5 and 20 hours.

When using a paratoluene sulfonic acid catalyst, the reaction temperature range may vary from 115° C. (reflux at atmospheric pressure) using a toluene solvent up to 200° C. (reflux, preferably using a toluene or xylene solvent at higher pressures). Thus, the reaction temperature range is considerably greater in scope when using the paratoluene sulfonic acid catalyst than when using the potassium acid sulfate catalyst. Furthermore, the solvent used may be toluene, xylene or a heavy hydrocarbon mineral oil so long as the solvent is inert to the reaction product and is inert to the reactant.

Significantly, the use of the paratoluene sulfonic acid catalyst carries with it a certain definitive advantage over the use of all other dehydration catalysts including the potassium acid sulfate; that is, the versatility of equipment that can be used with paratoluene sulfonic acid as opposed to, for example, potassium acid sulfate. The paratoluene sulfonic acid catalyst's use gives rise to insignificant corrosion problems when using steel reactors. Thus, when using a paratoluene sulfonic acid catalyst, the need for using glass-lined equipment or glass-lined reactors is obviated thereby significantly reducing the capital equipment cost in the establishment of a plant for producing the farnesene isomer mixtures of this invention. On the other hand, when using the potassium acid sulfate catalyst, although this catalyst gives rise to useful, unobvious and advantageous products, it is necessary to devise such equipment whereby little corrosion takes place during the course of the reaction. Such equipment will necessarily be either stainless steel or, more preferably, glass-lined equipment with appropriate accessories. When carrying out these reactions in a continuous fashion, it is much more important to design equipment whereby the corrosion incidence will be minimal thereby requiring specific low acid environment corrosion type alloys. The situation concerning the use of continuous equipment gives rise to an even greater need to use either specific alloys when utilizing a potassium acid sulfate catalyst or utilizing a paratoluene sulfonic acid catalyst whereby standard continuous steel processing equipment may be utilized.

Significantly, whether using a potassium acid sulfate catalyst or a paratoluene sulfonic acid catalyst, no nerolidol acetates will be formed which is the case when using, for example, an acetic anhydride dehydration catalyst. The structures of the nerolidol esters are, when using an acetic anhydride catalyst:

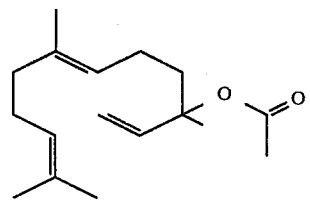

(E isomer) and

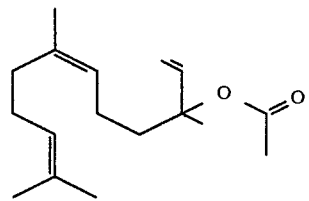

(Z isomer).

Whether using a potassium acid sulfate catalyst or a paratoluene sulfonic acid catalyst, the ratio of catalyst to nerolidol may vary from 1:1000 (wt/wt) up to 1:5 with a preferred ratio of 1:60 when using the potassium acid sulfate catalyst and a preferred ratio of 1:500 when using the paratoluene sulfonic acid catalyst. The concentration of catalyst in the reaction mixture may vary from 1:2000 up to 1:100 with a preferred ratio of between 1:800 and 1:1,500 (wt/wt) being optimum.

The ratio of solvent:nerolidol isomer mixture varies depending upon the particular solvent used and the desired catalyst concentration. Thus, when using a heavy hydrocarbon inert mineral oil and a potassium acid sulfate catalyst, the preferred ratio of solvent:nerolidol isomer reactants is between 1:1 and 1:4 with a most preferred ratio being 1:3. When using a toluent solvent or a xylene solvent, the preferred weight/weight ratio may vary from 1:2 up to 2:1 with a most preferred weight ratio of nerolidol isomer mixture:solvent being 1:1.

It will be appreciated from the present disclosure that the product-by-process of our invention, the farnesene isomer mixture, can be used to alter, vary, fortify, modify, enhance or otherwise improve the organoleptic properties including flavor and/or aroma of foodstuffs, chewing gums, medicinal products and toothpastes.

The terms "alter" and "modify" in their various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

The term "enhance" is used herein to mean the intensification of a flavor or aroma characteristic or note without the modification of the quality thereof. Thus, "enhancement" of a flavor or aroma means that the enhancement agent does not add any additional flavor note.

Such farnesene isomer mixtures are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the farnesene isomer mixture according to this invention is used in a flavoring composition, it can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, convenitonal materials can be used and broadly include other flavor materials, vehicles, stabilizers, thickeners, surface active agents, conditioners and flavor intensifiers.

Such conventional flavoring material include saturated, unsaturated, fatty and amino acids; alcohols, including primary and secondary alcohols; esters, carbonyl compounds, including ketones and aldehydes; lactones; cyclic organic materials including benzene derivatives, alicyclics, heterocyclics such as furans, thiazoles, thiazolidines, pyridines, pyrazines and the like; other sulfur-containing materials including thiols, sulfides, disulfies and the like; proteins; lipids; carbohydrates; so-called flavor potentiators such as monosodium glutamate guanylates, and inosinates; natural flavoring materials such as cocoa, vanilla, and caramel; essential oils and extracts such as anise oil, clove oil and the like; artificial flavoring materials such as vanillin; and the like.

It has been found in certain preferred embodiments that various adjuvants are particularly suited for use with various alkenal derivatives according to the present invention. In view of the utility of compounds according to the present invention for fruit, citrus, vegetable, beverage, and confectionary flavors and for enhancing such flavors, it is preferred in certain embodiments that the farnesene isomer mixture according to this invention be combined with one or more adjuvants such as maltol, ethyl maltol, ethyl acetate, ethyl butyrate, ethyl propionate, propanal, n-decanal, 3-hexanol, n-octanal, n-nonanal, citral, fusel oil, n-hexanal, n-butanol, d-limonene, linalool, citronellal, n-dodecanal, 2-alkylidene alkenal, e.g., 2-ethylidenecis-3-hexenal, trans-2-propenyl-trans-2-pentenal and 2-ethylidene-trans-3-hexenal, geraniol, nerol, or vanillin.

Stabilizers include preservatives such as sodium chloride and the like, antioxidants such as calcium and sodium ascorbate, ascorbic acid, butylated hydroxyanisole, butylated hydroxytoluene, propyl gallate and the like, sequestrans such as citric acid, EDTA, phosphates, and the like.

Thickeners include carriers, binders, protective colloids, suspending agents, emulsifiers, and the like, such as agar,agar, carrageenan, celluloe and cellulose derivatives such as carboxymethyl cellulose and methyl cellulose, and the like, and other proteinaceous materials, lipids, carbohydrates, starches and pectins.

Surface active agents include emulsifying agents such as mono- and/or diglycerides of fatty acids including capric acid, caprylic acid, palmitic acid, myristic acid, oleic acid, and the like, lecithin, defoaming and flavor-dispersing agents such as sorbitan monostearate, potassium stearate, hydrogenated tallow alcohol, and the like.

Conditioners include compounds such as bleaching and maturing agents such as benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents such as sodium acetate, ammonium bicarbonate, ammonium phosphate, citric acid, lactic acid, vinegar and the like; colorants such as carminic acid, cochineal, turmeric, curcumin, approved food and drug dyes, and the like; firming agents such as aluminum sodium sulfate, calcium chloride and calcium gluconate; texturizers; anticaking agents such as aluminum calcium sulfate and tribasic calcium phosphate; enzymes; yeast foods such as calcium lactate and calcium sulfate; nutrient supplements such as iron salts including ferric phosphate, ferric pyrophosphate, ferrous gluconate and the like, riboflavin, vitamins, zinc sources such as zinc chloride, zinc sulfate, and the like.

The farnesene isomer mixture, or the compositions incorporating them, as mentioned above, can be combined with one or more vehicles or carriers for adding them to the particular product. Vehicles can be edible or otherwise suitable materials such as ethyl alcohol, propylene glycol, water, and the like. Carriers include materials such as gum arabic, carrageenan, other gums, and the like. The alkenal compounds according to this invention can be incorporated with the carriers by conventional means such as spary-drying, drum-drying, and the like. Such carriers can also include materials for coacervating the alkylidene alkenal derivatives (and other flavoring ingredients, as present) to provide encapsulated products. When the carrier is an emulsion, the flavoring composition can also contain emulsifiers such as mono- and diglycerides of fatty acids and the like. With these carriers or vehicles, the desired physical form of the composition can be prepared.

It will be understood by those skilled in the art that the farnesene isomer mixture according to the present invention can be added to the materials to be flavored at any convenient point in the production of the finished product. Thus, when the derivatives are used to alter or otherwise vary the flavor of the foodstuff, they can be added in the original mixture, dough, emulsion, batter, syrup, or the like prior to any cooking or heating operating. Alternatively, they can be added at a later stage of processing if volatilization losses would be excessive during the earlier processing.

When the derivatives are used to treat tobacco products for example, the additive can be applied in a suitable manner, as by spraying, dipping, or otherwise. They can be applied during the "casing" or final spray treatment of the tobacco, or they can be applied at some earlier stage of curing or preparation. The quantity of the farnesene isomer mixtures thereof utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff, tobacco product, or other consumable product; the amount and type of flavor initially present in the product; the further process or treatment steps to which the product will be subjected; regional and other preference factors; the type of storage, if any, to which the product will be subjected; and the preconsumption treatment, such as baking, frying, and so on, given to the product by the ultimate consumer. According, the terminology "effective amount" and "sufficient amount" is understood in the context of the present invention to be quantitatively adequate to alter the flavor of the foodstuffs, chewing gums, medicinal products and toothpastes or other consumable material.

It is preferred that the ultimate composition contain about 0.02 parts per million (ppm) up to about 150 ppm of the farnesene isomer mixture of our invention. More particularly, in food compositions it is desirable to use from about 0.05 ppm for enhancing flavors and in certain preferred embodiments of our invention, from about 0.2 up to about 50 ppm of the farnesene isomer mixture is included to add positive flavors to the finished product.

The amount of farnesene isomer mixture to be utilized in flavoring compositions can be varied over a wide range depending upon the particular quality to be added to the foodstuffs, chewing gums, medicinal products and toothpastes. Thus, amounts of the farnesene isomer mixture according to the present invention from about 2 ppm up to 80 to 90% can be incorporated in such compositions. It is generally found to be desirable to include from about 10 ppm up to about 0.1 percent of the farnesene isomer mixture in such compositions.

Examples I and III, following, serve to illustrate the process for producing the farnesene isomer mixture of our invention usable in practicing Example V and examples following Example V. Example II illustrates a process whereby α-farnesene isomers such as those having the structures:

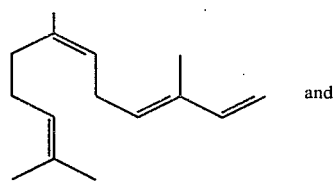

and

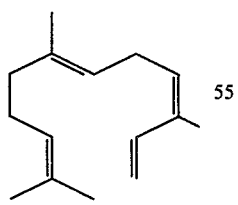

are isolated from the head space of magnolia. Example IV following, illustrates a process unworkable for the purposes of our invention using an acetic anhydride dehydrating agent producing, in addition to farnesene isomers, a mixture of isomers of farnesyl esters.

It will be understood that these examples are illustrative, and the invention is to be considered restricted thereto only as indicated in the appended claims.

All parts and percentages given herein are by weight unless otherwise specified.

EXAMPLE I

PREPARATION OF MIXTURE OF FARNESENE ISOMERS USING A POTASSIUM ACID SULFATE DEHYDRATION CATALYST

Reaction

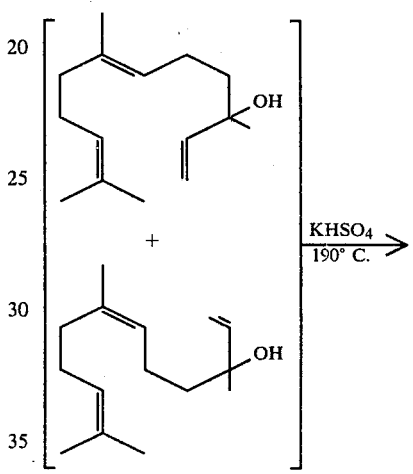

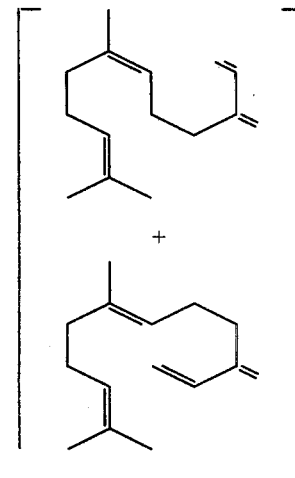

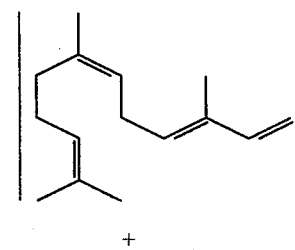

+

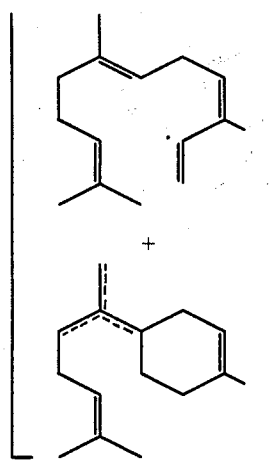

Into a five liter reaction flask equipped with stirrer, Rushover head, 1' splash column with glass packing, thermometer, addition funnel, glass "Y" tube, heating mantle and vacuum set-up, is placed 1000 grams of Primol ® (a mineral oil manufactured by the Exxon Corporation of Linden, N.J.) and 50 grams of potassium acid sulfate (KHSO₄). The resulting mixture is heated to 185° C. and maintained at 185° C. for a period of 15 minutes.

A mixture of nerolidol isomers defined according to the GLC profile set forth in FIG. "A" is placed in the addition funnel and, over a 10 hour period while maintaining the reaction mass temperature at 190° to 195° C. and maintaining a pressure above the reaction mass of 10-15 mm/Hg (vacuum), 3000 grams of the nerolidol isomer mixture is added to the potassium acid sulfate/Primol ® mixture at a rate equal to the rate of condensed distillate. Thus, the distillation of the farnesene isomer mixture is carried out simultaneously with the addition of the nerolidol to the dehydrating medium. The fractions collected are as follows:

| Fraction No. | Vapor Temp °C. | Liquid Temp °C. | Pressure MM Hg. | Wt (g) |
|---|---|---|---|---|
| 1 | 114/127 | 193/188 | 15/15 | 330.3 |
| 2 | 130 | 189 | 15 | 671.4 |
| 3 | 125 | 193 | 15 | 875.9 |
| 4 | 130 | 195 | 15 | 504.2 |
| 5 | 110 | 195 | 15 | 394.2 |
|   |   |   |   | 2776.0 g. |

After the addition is completed, the reaction mass is stirred at 190°-200° C. for 1 hour in order to insure complete recovery.

All fractions are bulked, diluted with anhydrous diethyl ether (500 ml), washed with one 1,000 ml portion of 5% sodium carbonate and dried over anhydrous magnesium sulfate. The resulting product is then evaporated on a rotary evaporator whereby the diethyl ether is evaporated.

FIG. 1 is the GLC profile after the base wash. (GLC conditions: 10'×⅛"5% Carbowax column programmed at 100°-220° C. at 4° C. per minute).

The base washed farnesene bulk (2776.0 grams) is strip distilled using a 2" Splash column containing glass Raschig rings as column packing, yielding the following fractions:

| Fraction No. | Vapor Temp °C. | Liquid Temp °C. | Pressure MM Hg. | Wt (g) |
|---|---|---|---|---|
| 1 | 83/93 | 117/122 | 1/1 | 496.7 |
| 2 | 94 | 123 | 1 | 583.6 |
| 3 | 96 | 128 | 1 | 658.2 |
| 4 | 109 | 139 | 1 | 596.2 |
| 5 | 125 | 205 | 1 | 265.8 |
|   |   |   |   | 2600.5 g. |

All fractions are then bulked (2600.5 grams) and fractionated on a 12" vacuum jacketed glass column containing glass Raschig rings as column packing, yielding the following fractions:

| Fraction No. | Vapor Temp°C. | Liquid Temp°C. | Pressure MM Hg. | Reflux Ratio | Wt (g) |
|---|---|---|---|---|---|
| 1 | 46/54 | 135/132 | 1.4/1.0 | 9:1 | 69.5 |
| 2 | 51 | 130 | 0.9 | 9:1 | 87.4 |
| 3 | 52 | 132 | 0.8 | 9:1 | 99.4 |
| 4 | 70 | 133 | 1.4 | 9:1 | 45.1 |
| 5 | 63 | 134 | 0.9 | 9:1 | 109.0 |
| 6 | 53/52 | 127/129 | 0.8/0.7 | 9:1 | 98.4 |
| 7 | 52 | 131 | 0.7 | 9:1 | 136.3 |
| 8 | 51 | 130 | 0.7 | 9:1 | 117.1 |
| 9 | 52 | 133 | 0.7 | 9:1 | 151.2 |
| 10 | 52 | 135 | 0.7 | 9:1 | 166.3 |
| 11 | 62/61 | 133/133 | 0.7/0.7 | 9:1 | 88.8 |
| 12 | 81 | 145 | 2.0 | 9:1 | 68.7 |
| 13 | 71 | 130 | 2.0 | 9:1 | 91.2 |
| 14 | 73 | 132 | 2.0 | 9:1 | 94.1 |
| 15 | 65/73 | 130/131 | 1.2/1.1 | 9:1 | 58.8 |
| 16 | 61 | 129 | 1.2 | 9:1 | 79.1 |
| 17 | 73 | 131 | 1.2 | 9:1 | 141.6 |
| 18 | 62 | 137 | 0.6 | 9:1 | 116.5 |
| 19 | 50/59 | 133/138 | 0.7/0.6 | 9:1/4:1 | 99.8 |
| 20 | 63 | 138 | 0.6 | 3:2 | 119.5 |
| 21 | 45 | 204 | 1.4 | 3:2 | 87.2 |
|   |   |   |   |   | 2125.0 g |

Fractions 4–18 (1562.2 grams) are bulked.

FIG. 2 is the GLC profile for bulked fractions 4–18.

In FIG. 2, peak 11 indicates the compound having the structure:

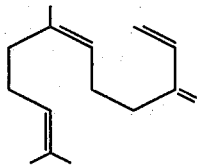

Peak 12 indicates the compound having the structure:

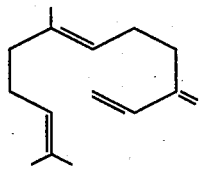

Peak 13 indicates the compound having the structure:

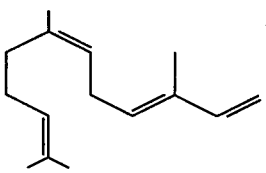

Peak 14 indicates the compounds having the structures:

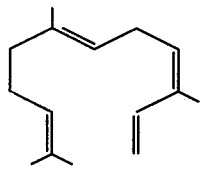 and 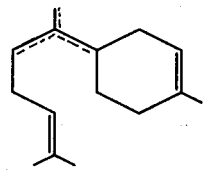

wherein the structure:

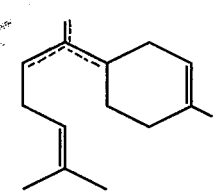

one of the dashed lines represents a pi double bond and each of the other dashed lines represent single bonds. Peaks 15A and 15B are indicative of the compounds having the structures:

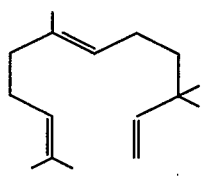 and 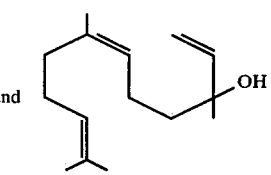

the isomers of nerolidol.

FIGS. 3, 4, 5 and 6 are infra-red spectra of, respectively, peaks 11, 12, 13 and 14 of FIG. 2.

FIGS. 7, 8, 9 and 10 are, respectively, NMR spectra for peaks 11, 12, 13 and 14 of FIG. 2.

FIGS. 11, 12, 13 and 14 are, respectively, mass spectra for peaks 11, 12, 13 and 14 of FIG. 2.

Bulked fractions 14–18 have a very natural fresh green, herbaceous aroma with citrusy (lemon/lime) undertones, from a food flavor standpoint.

EXAMPLE II

ISOLATION OF α-FARNESENE ISOMER MIXTURE FROM MAGNOLIA HEADSPACE

The volatiles of two magnolia blossoms (Cadiz, Spain) were entrained on Carbowax 20 by sweeping the petals with helium for 24 hours. The trap is then analyzed by GLC analysis on a 500'×0.03" SF-96 capillary column.

Figure 16A:
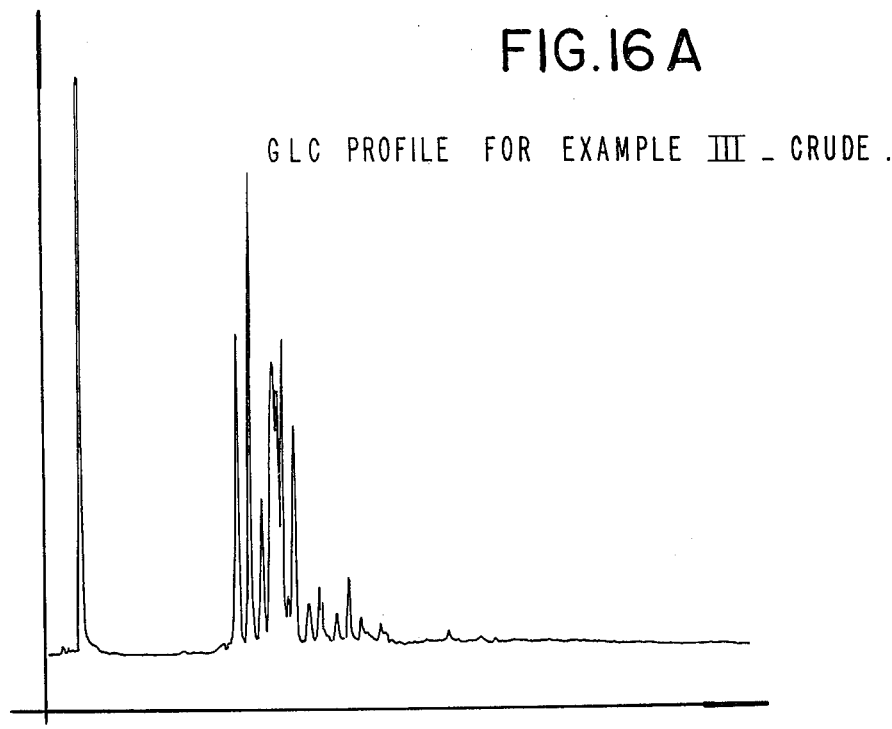
FIG. 16(A) is the GLC profile for the crude reaction product of Example III.
Figure 16B:
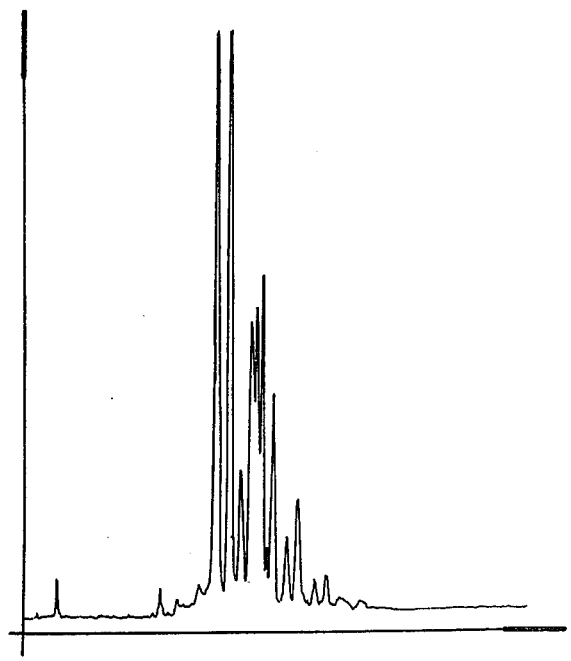
FIG. 16(B) is the GLC profile for fraction 1 of the distillation product of the reaction product of Example III.
Figure 16C:
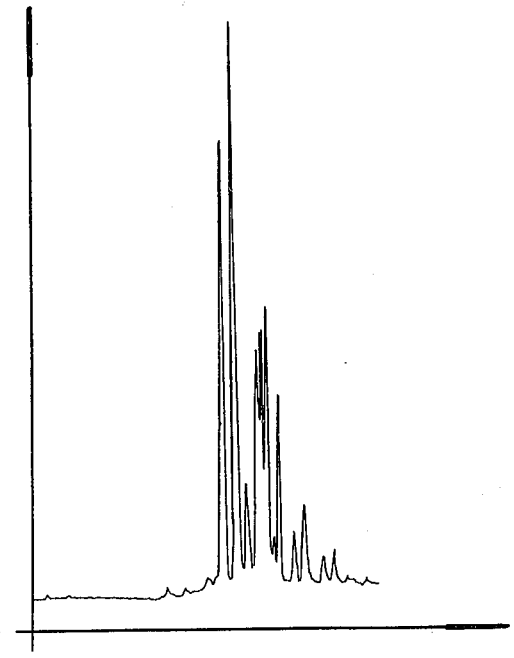
FIG. 16(C) is the GLC profile for fraction 2 of the distillation product of the reaction product of Example III.
Figure 16:
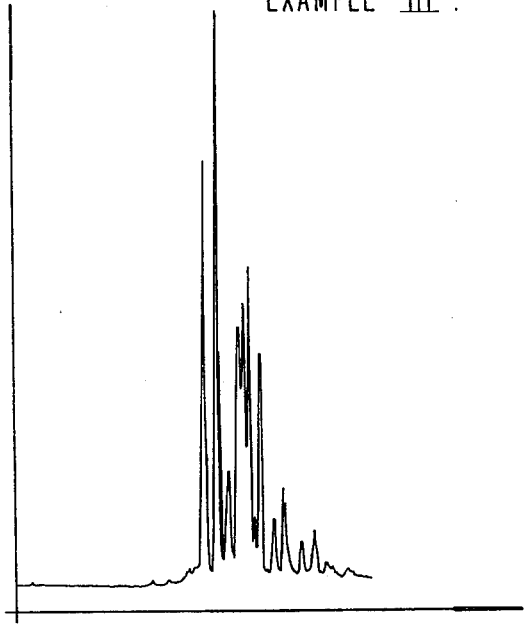
FIG. 16(D) is the GLC profile for fraction 3 of the distillation product of the reaction product of Example III.
FIG. 16(E) is the GLC profile for fraction 4 of the distillation product of the reaction product of Example III.
FIG. 16(F) is the GLC profile for fraction 5 of the distillation product of the reaction product of Example III.
FIG. 16(G) is the GLC profile for fraction 6 of the distillation product of the reaction product of Example III.
FIG. 16(H) is the GLC profile for fraction 7 of the distillation product of the reaction product of Example III.
FIG. 16(J) is the GLC profile for fraction 8 of the distillation product of the reaction product of Example III.
FIG. 16(K) is the GLC profile for fraction 9 of the distillation product of the reaction product of Example III.
FIG. 16(L) is the GLC profile for bulked fractions 4-7 of the distillation product of the reaction product of Example III.
Figure 16:
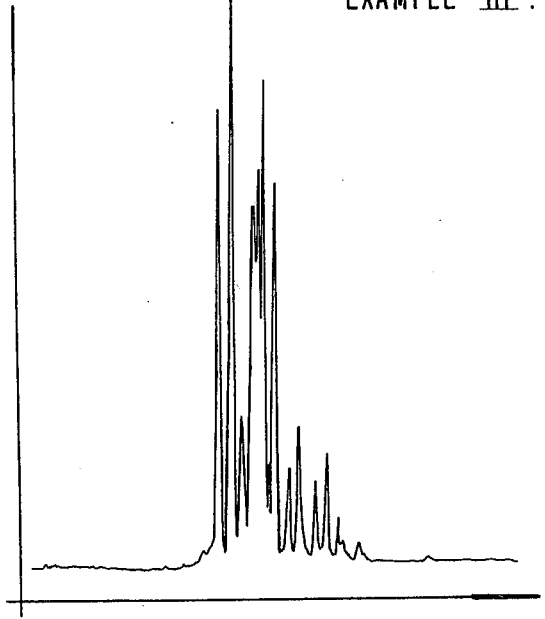
Figure 16:
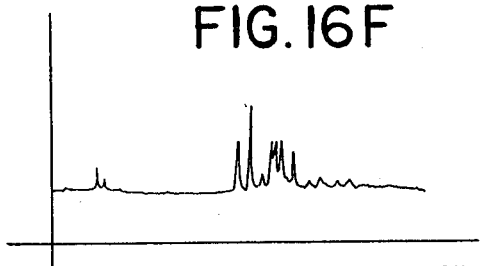
Figure 16:
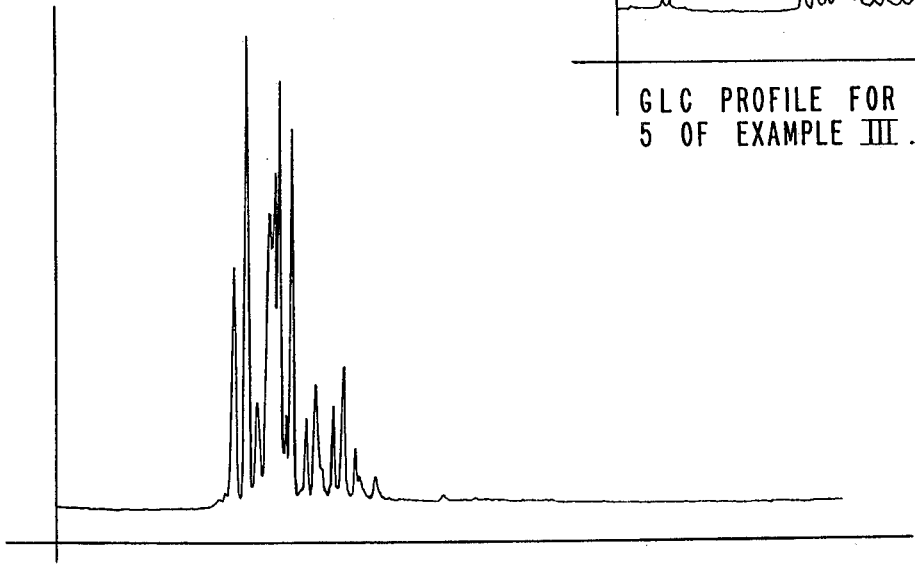

FIG. 16 is the GLC profile for this headspace. Reference numeral 16 is indicative of the α-farnesene isomers contained in the headspace. Such α-farnesene isomers are represented by the structures:

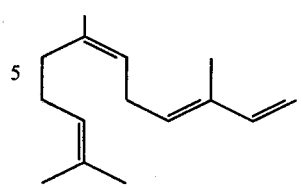 and

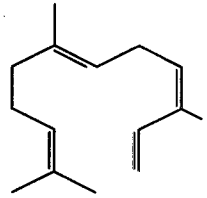

EXAMPLE III

PREPARATION OF ISOMERIC FARNESENE MIXTURE FROM NEROLIDOL MIXTURE USING PARATOLUENE SULFONIC ACID CATALYST

Reaction

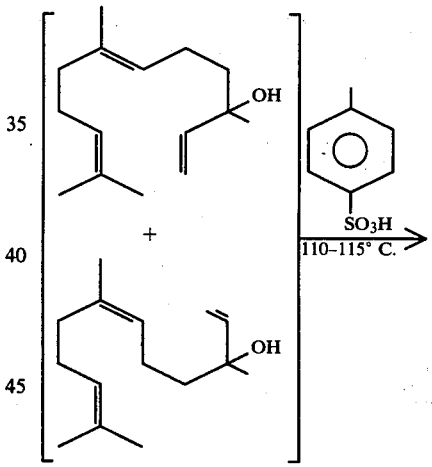

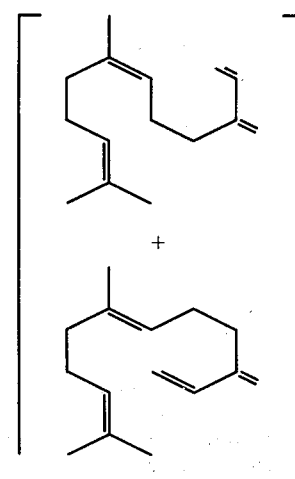

-continued

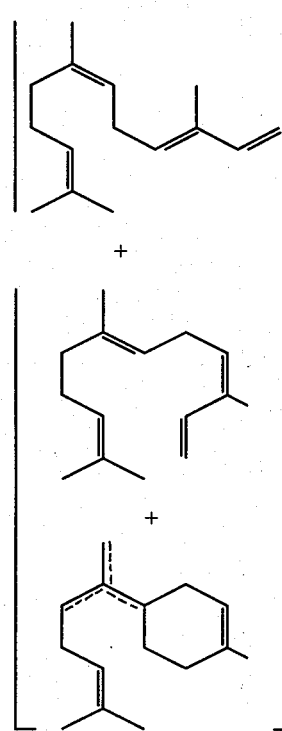

(wherein in the structure:

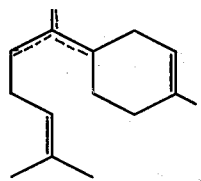

one of the dashed lines is indicative of a pi double bond and each of the other of the dashed lines is indicative of single bonds, said structure:

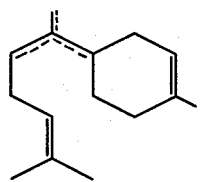

being indicative of a mixture of three compounds).

Into a two liter, three-neck reaction flask equipped with mechanical stirrer, reflux condenser, Bidwell water separator, thermometer and heating mantle is added 500 grams of a nerolidol isomer mixture containing compounds having the structures:

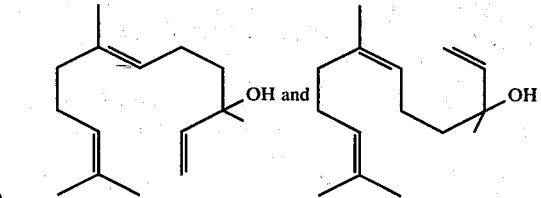

defined more specifically according to the GLC profile of FIG. B, and one gram of paratoluene sulfonic acid.

The reaction mass is stirred at room temperature for a period of 2 hours. The reaction mass is then refluxed for a period of 3 hours until 40 ml of water is removed. The reaction mass is then washed with one portion of 200 ml of 5% sodium carbonate and two 100 ml portions of water. The resulting organic layer is dried over anhydrous magnesium sulfate, filtered and the solvent is removed at atmospheric pressure.

The crude reaction mass is then analyzed on a GLC column.

FIG. 16(A) is the GLC profile for the crude product. (Conditions: 10'×⅛"5% Carbowax column programmed at 100°-240° C. at 4° C. per minute.)

The crude reaction mass is then distilled using a 4" column containing glass rings as packing and a Rushover head.

The distillation fractions are as follows:

| Fraction Number | Vapor Temp. (°C.) | Liquid Temp. (°C.) | Pressure mm/Hg. | Weight of Fraction (grams) |
|---|---|---|---|---|
| 1 | 82/85 | 103/104 | 1.8/1.8 | 22.8 |
| 2 | 87 | 104 | 1.8 | 33.6 |
| 3 | 89 | 105 | 1.8 | 51.3 |
| 4 | 89 | 108 | 1.8 | 51.1 |
| 5 | 90 | 111 | 1.8 | 50.6 |
| 6 | 90 | 115 | 1.8 | 46.6 |
| 7 | 92 | 118 | 1.8 | 51.1 |
| 8 | 94 | 155 | 1.8 | 22.4 |
| 9 | 100 | 200 | 1.8 | 11.5 |

Fractions 4-7 are bulked. These fractions have a pleasant fresh green, herbaceous aroma with citrusy (lemon/lime) undertones, from a food flavor standpoint.

FIG. 16(B) is the GLC profile for fraction 1 of the foregoing distillation (conditions: 10'×⅛"5% Carbowax column programmed at 100°-220° C. at 4° C. per minute). The conditions for the following GLC analysis are the same.

Figure 16H:
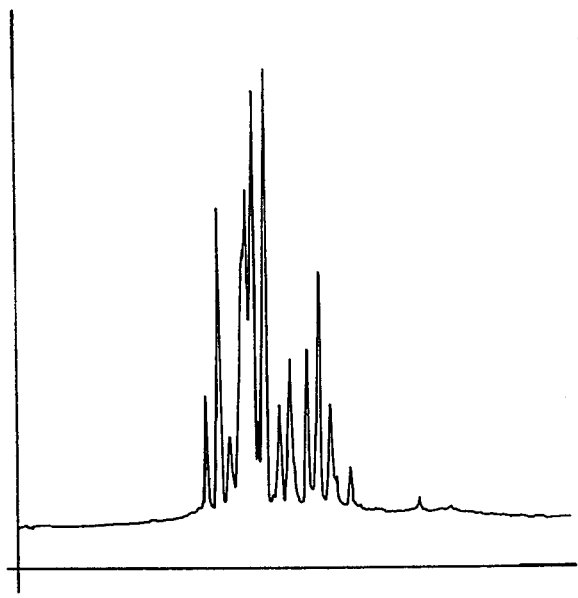
Figure 16J:
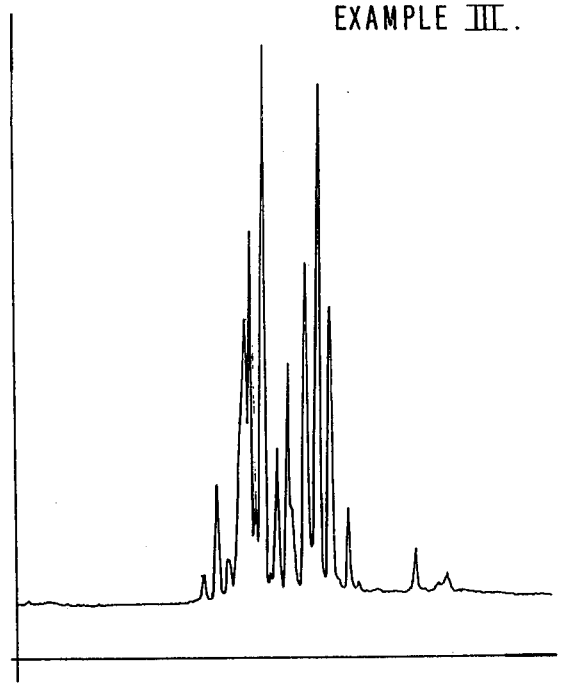
Figure 16K:
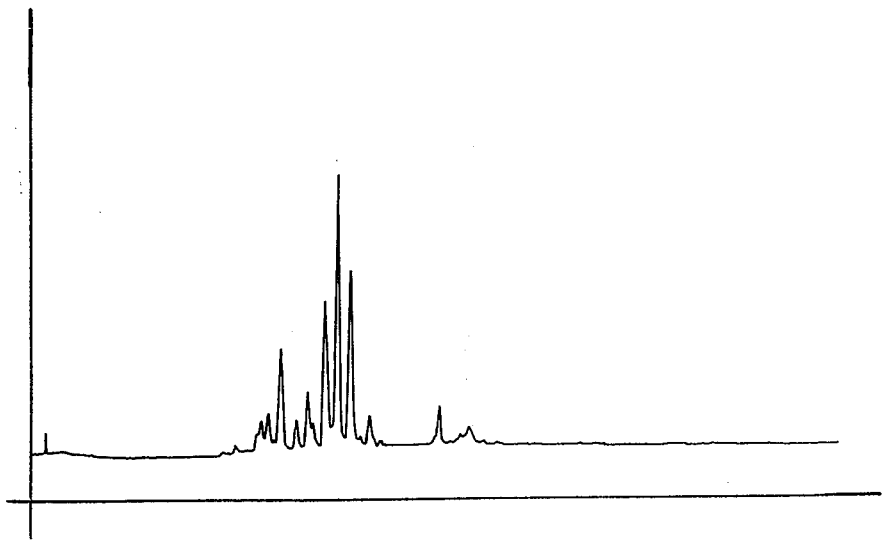
Figure 16L:
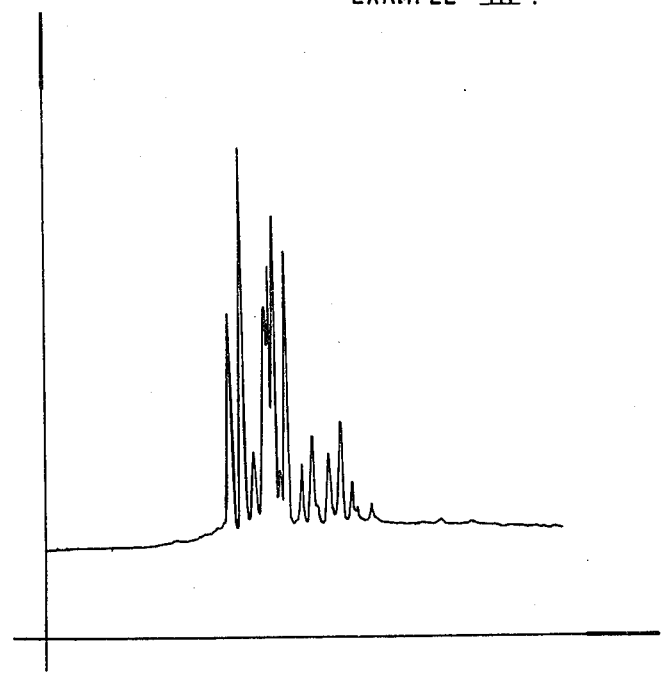

FIG. 16(C) is the GLC profile for fraction 2.
FIG. 16(D) is the GLC profile for fraction 3.
FIG. 16(E) is the GLC profile for fraction 4.
FIG. 16(F) is the GLC profile for fraction 5.
FIG. 16(G) is the GLC profile for fraction 6.
FIG. 16(H) is the GLC profile for fraction 7.
FIG. 16(J) is the GLC profile for fraction 8.
FIG. 16(K) is the GLC profile for fraction 9.
FIG. 16(L) is the GLC profile for bulked fractions 4-7.

Figure 17:
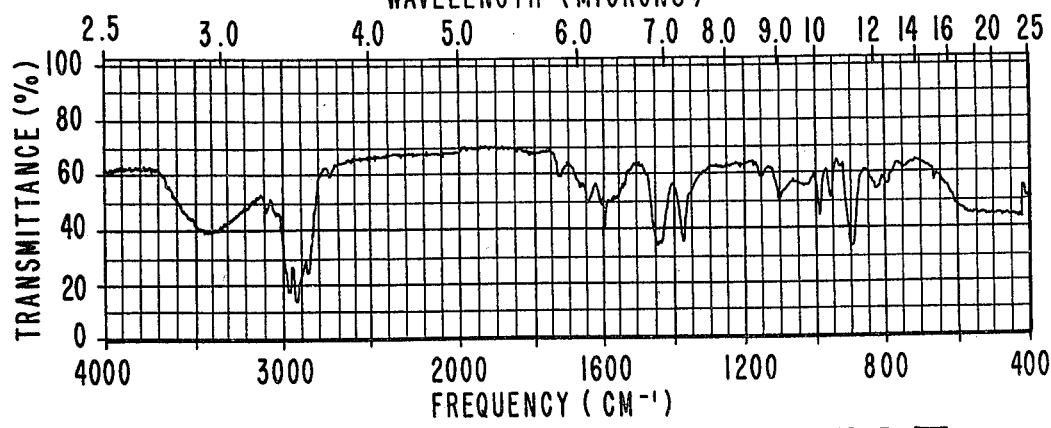
FIG. 17 is the infra-red spectrum for bulked fractions 4-17 of the distillation product of the reaction product of Example III.

FIG. 17 is the infra-red spectrum for bulked fractions 4-7 of the foregoing distillation.

EXAMPLE IV

ATTEMPTED PREPARATION OF AROMA AND TASTE ACCEPTABLE MIXTURE OF FARNESENE ISOMERS

Into a one-liter distillation flask equipped with thermometer, condenser, separatory funnel (containing dry ice), magnetic stirrer and heating mantle under a nitrogen atmosphere is placed 200 grams of nerolidol, a 65:35 mixture of the isomers having the structures:

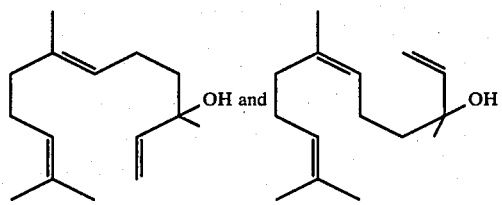

obtained from the Givaudan Corporation of Clifton, N.J. and 500 ml acetic anhydride. The reaction mass is refluxed at 130°-140° C. for a period of 4 hours.

The reaction mass is then added to 300 grams of ice in a separatory funnel.

The organic layer and the aqueous layer are separated. The organic layer is washed with a 10% solution of sodium carbonate followed by saturated sodium chloride solution. The organic layer is dried over anhydrous magnesium sulfate and the solvent is evaporated on a rotary evaporator.

The weight of the crude material is 237.8 grams.

The resulting crude material is distilled on a Spinning Band column yielding the following fractions:

| Fraction Number | Vapor Temp. (°C.) | Liquid Temp. (°C.) | Pressure mm/Hg. | Weight of Fraction (grams) |
| --- | --- | --- | --- | --- |
| 1 | 88/101 | 148/15D | 20/20 | 2.0 |
| 2 | 102 | 151 | 20 | 3.2 |
| 3 | 103 | 151 | 20 | 3.0 |
| 4 | 102 | 151 | 19 | 2.4 |
| 5 | 106 | 159 | 20 | 3.8 |
| 6 | 111 | 151 | 20 | 3.5 |
| 7 | 115 | 155 | 20 | 3.4 |
| 8 | 70 | 160 | ? | 2.5 |
| 9 | 103/112 | 161/161 | 20/20 | 3.6 |
| 10 | 111 | 161 | 20 | 3.6 |
| 11 | 110 | 161 | 20 | 3.6 |
| 12 | 106 | 166 | 20 | 3.2 |
| 13 | 93 | 166 | 20 | 3.1 |
| 14 | 93 | 166 | 20 | 3.1 |
| 15 | 102 | 168 | 20 | 2.3 |
| 16 | 102 | 168 | 20 | 2.7 |
| 17 | 100 | 170 | 20 | 2.4 |

Fractions 6-12 are then re-distilled on a Micro-Vigreux column to yield the following fractions:

| Fraction Number | Vapor Temp. (°C.) | Liquid Temp. (°C.) | Pressure mm/Hg. | Weight of Fraction (grams) |
| --- | --- | --- | --- | --- |
| 1 | 83/111 | 95/115 | 1.1/0.9 | 3.0 |
| 2 | 105 | 113 | 0.5 | 3.3 |
| 3 | 95 | 110 | 0.5 | 2.2 |
| 4 | 85 | 98 | 0.5 | 2.7 |
| 5 | 76 | 93 | 0.5 | 1.9 |
| 6 | 78 | 98 | 0.5 | 2.3 |
| 7 | 79 | 98 | 0.5 | 2.4 |
| 8 | 75 | 110 | 0.5 | 2.1 |
| 9 | 50 | 190 | 0.5 | 0.6 |

Fractions 4-8 are bulked and odor evaluated.

FIG. 18 is the GLC profile for the crude reaction product (conditions: 10'×⅛"5% Carbowax column programmed at 220° C. isothermal).

FIG. 19 is the GLC profile for bulked fractions 4-8 of the foregoing distillation (condtions: 10'×⅛"5% Carbowax column programmed at 200° C. isothermal).

In FIG. 18, the peaks 17A and 17B are indicative of farnesene isomers whereas peaks 18A, 18B and 18C are indicative of farnesyl acetate isomers as indicated by the structures:

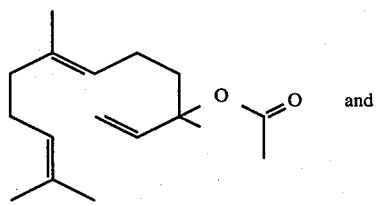

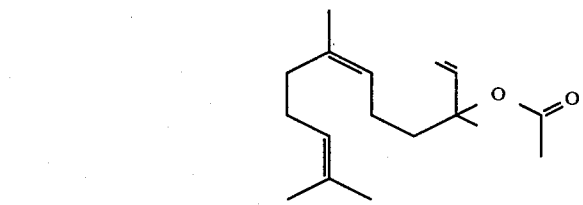

More particularly, in FIG. 19, peak 19A signifies the compound having the structure:

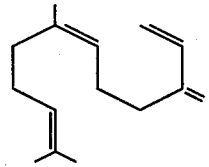

Peak 19B signifies the compound having the structure:

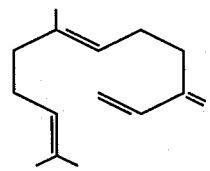

Peak 19C signifies the compound having the structure:

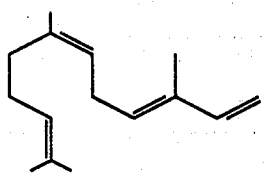

Peak 19D signifies the compound having the structure:

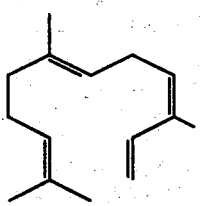

Insofar as the proportions of isomers in fractions 1-9 are concerned, these are as follows:

| Fraction Number | Weight (grams) | Peak 19A | Peak 19B | Peak 19C | Peak 19D |
|---|---|---|---|---|---|
| 1 | 3.0 | 10.8 | 22.8 | 16.1 | 31.4 |
| 2 | 3.3 | 9.6 | 21.6 | 16.5 | 33.5 |
| 3 | 2.2 | 8.3 | 20.4 | 16.6 | 36.0 |
| 4 | 2.7 | 8.0 | 20.0 | 16.6 | 37.0 |
| 5 | 1.9 | 7.6 | 19.6 | 16.7 | 37.5 |
| 6 | 2.3 | 6.1 | 17.5 | 16.4 | 38.4 |
| 7 | 2.4 | 4.4 | 15.1 | 17.0 | 44.7 |
| 8 | 2.1 | 2.9 | 11.7 | 16.0 | 49.0 |
| 9 | 0.6 | 1.3 | 7.6 | 13.4 | 49.0 |

The resulting bulked fractions 4-8 have a fresh, smooth, rosy, citrus note and the citrus part has a lemon/lime petitgrain aroma which is very intense. However, also present are strong terpenic notes. The material has none of the "fresh" aroma and taste nuances of the materials produced according the processes of Example I and III. In addition, the material produced according to the instant example has fatty, orangy, licorice-like, and metallic undertones which cause it to lack usefulness in substantially all flavor areas including foodstuff flavor areas.

EXAMPLE V

ELUCIDATION OF RANGE OF OPERABLE VARIABLES OF INVENTION

EXAMPLE V(A)

PRODUCTION OF FARNESENE ISOMER MIXTURE USING POTASSIUM ACID SULFATE CATALYST AT 150° C.

Reaction

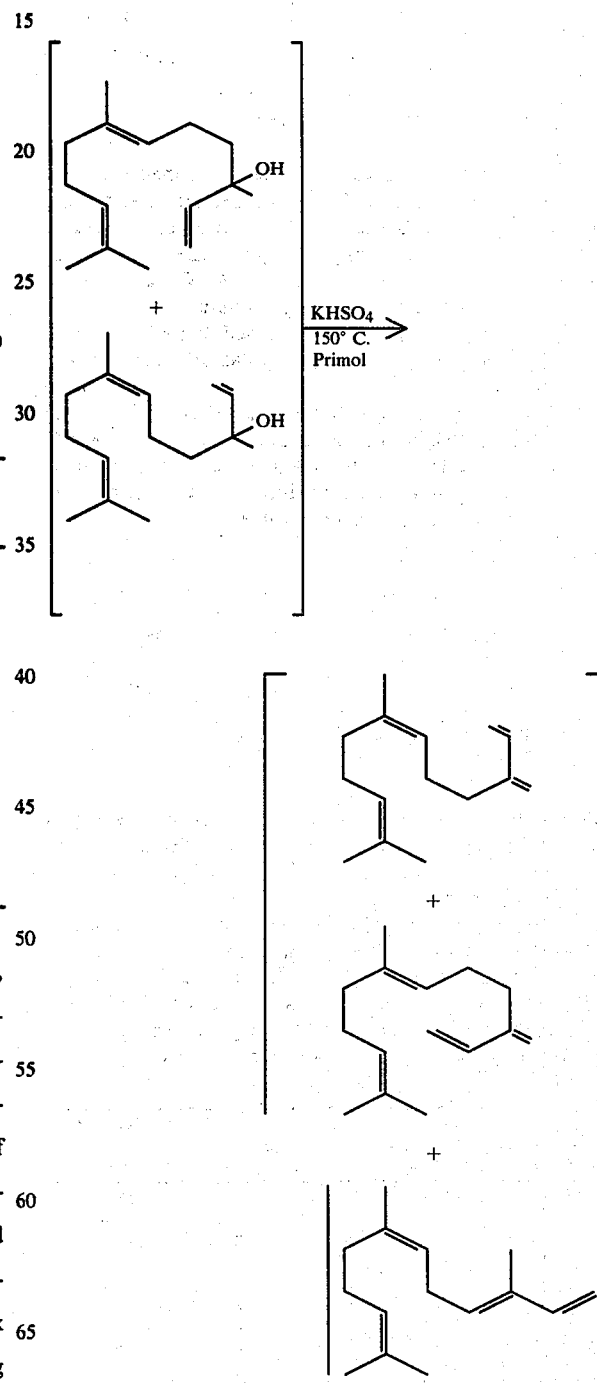

Into a three liter reaction vessel equipped with 6" Splash column Rushover head, mechanical stirrer, addition funnel, thermometer, and fraction cutter, is placed 500 grams Primol and 50 grams potassium acid sulfate (KHSO₄). The mixture is heated to 190° C. while keeping the system under 5 mm/Hg vacuum.

The resulting mixture is maintained at 190° C. for 30 minutes in order to "melt" the potassium acid sulfate crystals.

The resulting mixture is then cooled to 150° C. and over a period of 6 hours nerolidol having a GLC profile as set forth in FIG. A is added to the reaction mass dropwise from the addition funnel. The isomers of nerolidol in the nerolidol reactant are:

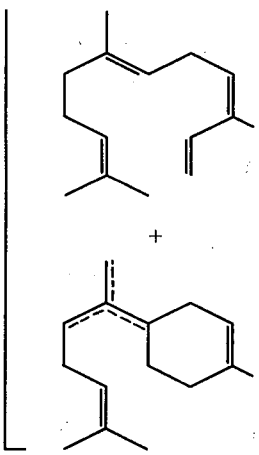

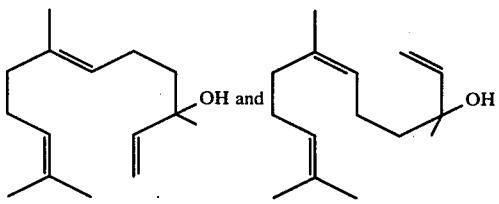

The addition rate of the nerolidol is adjusted to equal the "take off rate" of the product. After the addition is completed, the heating is continued until no additional liquid is distilled.

The reaction mass is then rinsed with toluene into a separatory funnel. The resulting organic layer is washed with 1 volume of 5% sodium carbonate and 2 volumes of water. The organic layer is then dried over anhydrous magnesium sulfate and stripped distilled and rushed over yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 74/90 | 92/97 | 3 | 75.4 |
| 2 | 91 | 98 | 2 | 79.3 |
| 3 | 92 | 100 | 2 | 92.9 |
| 4 | 93 | 100 | 2 | 81.7 |
| 5 | 93 | 100 | 2 | 86.5 |
| 6 | 96 | 104 | 2 | 88.0 |
| 7 | 99 | 106 | 2 | 88.0 |
| 8 | 101 | 108 | 2 | 95.2 |
| 9 | 103 | 109 | 2 | 86.9 |
| 10 | 103 | 109 | 2 | 89.1 |
| 11 | 103 | 109 | 2 | 83.9 |
| 12 | 103 | 112 | 2 | 85.7 |
| 13 | 103 | 114 | 2 | 81.5 |
| 14 | 112 | 145 | 2 | 86.3 |
| 15 | 155 | 210 | 2 | 51.3 |

Fractions 7-11 are bulked and have an intense fresh green, herbaceous aroma and taste profile with fresh citrusy (lemon/lime) undertones. The "fresh green" aroma and taste nuances are unique.

EXAMPLE V(B)

ATTEMPTED PRODUCTION OF FARNESENE ISOMERS USING CYCLOHEXANE SOLVENT AND POTASSIUM ACID SULFATE CATALYST

Into a 3 liter reaction flask equipped with thermometer, condenser, bidwell trap, mechanical stirrer and heating mantle is placed 1000 grams (4.5 moles) of nerolidol having a GLC profile in accordance with FIG. A, 20.0 grams of potassium acid sulfate and 600 ml cyclohexane. The resulting mixture is heated to reflux and 4.5 moles (80 grams) of water are collected. The refluxing proceeds for a period of 4 hours. At the end of the refluxing, the reaction mass is washed with 1 volume of 5% sodium carbonate and 1 volume of water. The reaction mass is then dried over anhydrous magnesium sulfate and stripped atmospherically to yield 920 grams of crude product. The resulting crude product is then distilled on a 2 liter-short Splash column packed with saddles to yield the following fractions:

| Fraction Number | Vapor Temp. (°C.) | Liquid Temp. (°C.) | Pressure mm/Hg. | Weight of Fraction (grams) |
|---|---|---|---|---|
| 1 | 78/87 | 101/108 | 0.95/0.90 | 78.7 |
| 2 | 88 | 111 | 0.90 | 83.8 |
| 3 | 89 | 111 | 0.9 | 82.5 |
| 4 | 89 | 115 | 0.9 | 100.8 |
| 5 | 89 | 126 | 0.9 | 95.1 |
| 6 | 112 | 158 | 0.9 | 85.5 |
| 7 | 120 | 181 | 1.1 | 83.2 |
| 8 | 120 | 205 | 1.1 | 94.6 |
| 9 | 123 | 214 | 1.1 | 68.6 |
| 10 | 112 | 225 | 1.0 | 32.5 |

The resulting product has a terpenic character and is unsuitable for use in augmenting or enhancing the aroma or taste of foodstuffs, chewing gums, medicinal products and toothpastes. It does not have the "fresh green" aroma found in the reaction product of Example V(A), I or III.

EXAMPLE V(C)

ATTEMPTED PRODUCTION OF FARNESENE ISOMERS USING TOLUENE SOLVENT AND POTASSIUM BISULFATE DEHYDRATING CATALYST

Into a 5 liter reaction flask equipped with mechanical stirrer, heating mantle, thermometer, bidwell trap and reflux condenser is placed 1000.0 grams (4.5 moles) of nerolidol having a GLC profile according to FIG. A, 600 ml tolune and 16.7 grams of potassium bisulfate (KHSO₄). The resulting mixture is heated to reflux (110° C.) and heating is continued until the theoretical amount of water, 81 grams (4.5 moles) are collected.

The water take-off proceeds for a period of 5.5 hours.

The reaction mass is then transferred to a 5 liter separatory funnel and 1000 ml of 5% sodium carbonate solution are added in order to wash the product. The organic and aqueous layers are then separated and the organic layer is dried over anhydrous magnesium sulfate. The resulting product is then filtered by gravity into a 3 liter distillation flask and rushed over on a short splash column packed with glass Raschig rings yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 25/30 | 40/68 | 20/5 | 107.1 |
| 2 | 98 | 112 | 2 | 99.5 |
| 3 | 100 | 115 | 2 | 103.4 |
| 4 | 100 | 117 | 2 | 103.0 |
| 5 | 100 | 120 | 2 | 85.6 |
| 6 | 100 | 128 | 2 | 99.9 |
| 7 | 100 | 138 | 2 | 98.5 |
| 8 | 108 | 179 | 2 | 63.8 |
| 9 | 110 | 205 | 2 | 85.9 |
| 10 | 150 | 225 | 2 | 37.9 |

The resulting product is then redistilled on an 18" glass column packed with Raschig rings to yield the following fractions:

| Fraction Number | Vapor Temp. (°C.) | Liquid Temp. (°C.) | Pressure mm/Hg. | Weight of Fraction (grams) |
|---|---|---|---|---|
| 1 | 64/68 | 113/120 | 1.2/1.1 | 42.7 |
| 2 | 70 | 121 | 1.1 | 60.4 |
| 3 | 70 | 122 | 1.0 | 77.3 |
| 4 | 73 | 127 | 1.1 | 64.6 |
| 5 | 74 | 128 | 1.1 | 80.9 |
| 6 | 76 | 130 | 1.2 | 93.6 |
| 7 | 85 | 135 | 1.6 | 88.4 |
| 8 | 78/84 | 138/140 | 1.1/1.1 | 38.9 |
| 9 | 92 | 177 | 1.0 | 93.3 |
| 10 | 93 | 215 | 1.6 | 54.3 |

The resulting product and each of the individual fractions are each incapable of being used for augmenting or enhancing the aroma or taste of foodstuffs, chewing gums, medicinal products or toothpastes in view of their terpinic, nerolidol-like character.

EXAMPLE VI

An orange flavor formulation is prepared by admixing:

| Ingredients | Parts by Weight |
|---|---|
| Natural orange oil | 13.00 |
| Acetaldehyde | 1.50 |
| Ethyl acetate | 0.10 |
| Ethyl butyrate | 0.50 |
| Propanol | 0.10 |
| trans-2-Hexenal | 0.10 |
| Ethyl alcohol (95%) | 60.00 |
| Fusel oil | 0.05 |
| Propylene glycol | 24.65 |

This is denominated Flavor A. A second formulation, Flavor B is prepared by adding a farnesene isomer mixture produced according to either of Examples I, III or V(A) (1 percent in ethanol) to a portion of Flavor A in a ratio of 2 parts to 100 parts of Flavor A.

Each of Flavors A and B is added in the amount of 2 ounces per gallon of 32° Baume sugar syrup to produce a syrup for combination with water to form a drink. The beverage prepared using Flavor A is a passable orange beverage of good character, flavor and intensity.

The beverage prepared using Flavor B has a much improved flavor. This improvement contributed by the farnesene isomer mixture is due to:
(i) a greater degree of the natural character of freshly squeezed orange juice;
(ii) an increase in the pulplike notes; and
(iii) greater orange juice flavor depth.

EXAMPLE VII

STRAWBERRY FLAVOR FORMULATION

A Strawberry flavor concentrate is prepared by admixing:

| Ingredients | Percent |
|---|---|
| Napthyl ethyl ether | 0.96 |
| Ethyl methyl phenyl glycidate | 2.88 |
| Vanillin | 2.66 |
| 2-Methyl-2-pentenoic acid | 3.90 |
| Ethyl acetate | 9.58 |
| Isoamyl butyrate | 12.25 |
| Ethyl butyrate | 26.20 |
| Isoamyl butyrate | 40.57 |
| 1-(Prop-1'-enyl)-3,4,5-trimethoxybenzene | 0.50 |
| Farnesene isomer mixture produced according to either of Examples I, III or V(A) | 0.85 |

The concentrate so prepared is dissolved in four times its volume or propylene glycol and the mixture is added to a simple syrup at the rate of 8 ounces per gallon of syrup.

The syrup is acidified by the addition of 1.5 ounces of 50% aqueous citric acid solution to each gallon of syrup. A carbonated beverage is prepared by mixing one ounce of the flavored acidified syrup with five ounces of carbonated water. The beverage so prepared has an excellent fresh strawberry flavor and is found to be markedly superior to a beverage prepared in the same manner but without the farnesene isomer mixture. The beverage prepared without the farnesene isomer mixture is found to be lacking in fresh green flavor notes present in natural strawberry flavor and aroma. Such fresh green notes are supplied by the farnesene isomer mixture.

EXAMPLE VIII

RASPBERRY FLAVOR

The following mixture is prepared:

| Ingredient | Parts by Weight |
|---|---|
| Para-hydroxy benzyl acetone | 5 |
| Vanillin | 2 |
| Maltol | 3 |
| Alpha-ione (1T solution in propylene glycol) | 15 |
| Isobutyl acetate | 15 |
| Ethyl butyrate | 5 |
| Ethyl acetate | 5 |
| Dimethyl sulfide (10% solution in propylene glycol) | 5 |
| Acetic acid | 15 |
| Acetaldehyde | 20 |
| Propylene glycol | 910 |

One of farnesene isomer mixtures produced according to either of Examples I, III or V(A) is added to the above mixture at rates of 0.02%, 0.04%, 0.06%, 0.1% and 0.15%. Flavor formulations with this derivative are then compared with a flavor formulation without the farnesene isomer mixture at the rate of 0.01% in water (100 parts per million) by a bench panel. The flavor formulation containing the farnesene isomer mixture has a strong delicate raspberry aroma with fresh green nuances which characteristics are not reproduced by the flavor formulation which does not contain said farnesene isomer mixture.

EXAMPLES IX

The following mixture is prepared:

| Ingredient | Parts by Weight |
| --- | --- |
| Natural Raspberry Concentrate Juice | 2½% |
| Water | 85% |
| Sugar syrup (37½° Baume) | 12½% |

The natural juice-like taste of this raspberry juice is imparted in increased strength by addition of one of the farnesene isomer mixtures prepared according to any of Examples I, III or V(A) at the rate of from 0.02 ppm up to 1.0 ppm.

EXAMPLE X

FLAVOR FORMULATION

The following mixture is prepared:

| Ingredients | Parts by Weight |
| --- | --- |
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 400 |

One of the farnesene isomer mixtures produced according to Examples I, III or V(A) is added to 975 grams of the above mixture which was then called "Test Composition". A control composition was prepared by adding 25 grams of additional lemon oil to 975 grams of the above mixture.

The test and control compositions were added to the food products described hereinafter and the proportions shown for 100 kelograms of material to be flavored.

| Ingredients | Parts by Weight |
| --- | --- |
| Cake | 20 grams |
| Pudding | 5-10 grams |
| Cooked sugar | 15-20 grams |

Cooked sugar-100 ml of sugar syrup (prepared by dissolving 1 kelogram of sucrose in 600 ml of water) and 20 grams of glucose were mixed together and slowly heated to 145° C. The flavor was added and the mass allowed to cool and harden.

Pudding-To 500 ml of warmed milk were added with stirring a mixture of 60 grams sucrose and 3 grams of pectin. The mixture was boiled for a few seconds and the flavor was added. The mixture was allowed to cool.

Cake-The following ingredients were mixed together:

| Ingredients | Grams |
| --- | --- |
| Vegetable margarine | 100 |
| Sodium chloride | 1.5 |
| Sucrose | 100 |
| Eggs | 2 |
| Flour | 100 |

The flavor was added and the mass was cooked for 40 minutes at 180° C. The finished foodstuff samples were tested by a panel of trained persons who had to express their views about the flavor of the samples. All members of the panel declared with no hesitation that the test samples had a more distinguished fresh fruit (kiwi fruit-like) note that the control samples and at the same time "a greenberry character".

EXAMPLE XI

A. Powder Flavor Composition

20 Grams of the flavor composition of Example VIII is emulsified in a solution containing 300 grams gum acacia and 70 grams water. The emulsion is spray-dried with a Bowen Lab Model Drier utilizing 260 c.f.m. of air with an inlet temperature of 500° F., an outlet temperature of 200° F., and a wheel speed of 50,000 rpm.

B. Sustained Release Flavor

The following mixture is prepared:

| Ingredients | Parts by Weight |
| --- | --- |
| Liquid raspberry flavor composition of Example VIII | 20.00 |
| Propylene glycol | 9.00 |
| Cab-O-Sil ® M-5 (Brand of Silica produced by the Cabot Corporation of 125 High Street, Boston, Mass. 02110; Physical Properties: Surface area: 200 m²/gm Nominal particle size: 0.012 microns Density: 2.3 lbs/cu.ft.) | 5.00 |

The Cab-O-Sil is dispersed in the raspberry flavor composition of Example VIII with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE XII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of the liquid flavor composition of Example VIII is added to the solution which is then homogenized to form an emulsion having particle size typically in the range of 5-40 microns. This material is kept at 120° F. under which conditions the gelatin will not jell.

Coacervation is induced by adding, slowly and uniformly 40 parts by weight of a 20% aqueous solution of sodium sulphate. During coacervation the gelation molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XIII
CHEWING GUM

100 Parts by weight of chicle are mixed with 4 parts by weight of the flavor prepared in accordance with Example XII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting raspberry flavor.

EXAMPLE XIV
CHEWING GUM

100 Parts by weight of chicle are mixed with 18 parts by weight of the flavor prepared in accordance with Example XIII. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting raspberry flavor.

EXAMPLE XV
TOOTHPASTE FORMULATION

The following separate groups of ingredients are prepared:

| Ingredients | Parts by Weight |
| --- | --- |
| GROUP "A" | |
| Glycerine | 30.200 |
| Distilled water | 15.325 |
| Sodium benzoate | .100 |
| Saccharin sodium | .125 |
| Stannous fluoride | .400 |
| GROUP "B" | |
| Calcium carbonate | 12.500 |
| Dicalcium phosphate (Dihydrate) | 37.200 |
| GROUP "C" | |
| Sodium N—Lauroyl Sarcosinate (foaming agent) | 2.000 |
| GROUP "D" | |
| Flavor Material of Example XII | 1.200 |
| | 100.000 (TOTAL) |

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium-n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant raspberry flavor, of constant strong intensity throughout said procedure (1–1.5 minutes).

EXAMPLE XVI
CHEWABLE VITAMIN TABLETS

The flavor material produced according to the process of Example XII is added to a Chewable Vitamin Tablet Formulation at a rate of 10 gm/Kg which chewable vitamin tablet formulation is prepared as follows:

In a Hobart Mixer, the following materials are blended to homogeneity:

| Ingredients | Gms/100 Tablets |
| --- | --- |
| Vitamin C (ascorbic acid) as ascorbic acid-sodium mixture 1:1 | 70.00 |
| Vitamin $B_1$ (thiamine mononitrate) as Rocoat ® 200 thiamine mononitrate 33⅓% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example XII | (as indicated above) |
| Certified lake color | 5.0 |
| Sweetener-sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 G dry Vitamin A acetate and 0.6 g Vitamin D are then added as beadlets. The entire blend is then compressed using concave punches at 0.5 g each.

Chewing of the resultant tablets yields a pleasant long-lasting, consistently strong raspberry flavor for a period of 12 minutes.

What is claimed is:

1. A process for augmenting or enhancing the aroma or taste of a consumable material selected from the group consisting of foodstuffs, chewing gums, toothpastes and medicinal products which comprises adding to said consumable material from about 0.02 ppm up to about 150 ppm based on the weight of said foodstuff of a farnesene isomer mixture produced according to the process of dehydrating a nerolidol isomer mixture containing nerolidol isomers defined according to the structures:

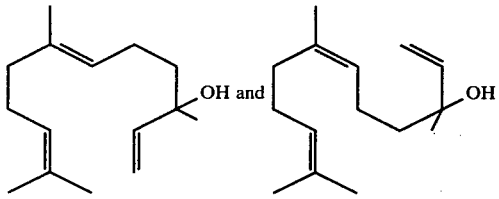

in the presence of a catalyst selected from the group consisting of potassium acid sulfate and paratoluene sulfonic acid at a temperature in the range of from 110° C. up to 200° C. and at a pressure in the range of from 1 mm/Hg pressure up to 200 atmospheres pressure, absolute during the reaction, simultaneously removing water of reaction from the reaction mass, and then distilling the resulting product at a temperature in the range of from 51° up to 103° C. and a pressure in the range of from 0.7 up to 2.0 mm/Hg, with the proviso that when a potassium acid sulfate catalyst is used, the temperature of reaction is in the range of 180°–200° C.; and with the further proviso that when using a paratoluene sulfonic acid catalyst, the reaction temperature is in the range of from 115° C. up to 200° C.

2. The process of claim 1 wherein the consumable material is a foodstuff.

3. The process of claim 1 wherein the consumable material is a chewing gum.

4. The process of claim 1 wherein the consumable material is a toothpaste.

5. The process of claim 1 wherein the consumable material is a medicinal product.

6. A food flavoring composition consisting essentially of (i) from about 2 ppm up to about 90% by weight of a farnesene isomer mixture produced according to the process of dehydrating an nerolidol isomer mixture containing nerolidol isomers defined according to the structures:

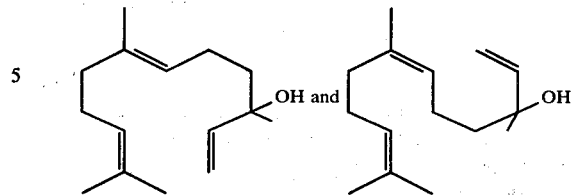

in the presence of a catalyst selected from the group consisting of potassium acid sulfate and paratoluene sulfonic acid at a temperature in the range of from 110° C. up to 200° C. and at a pressure in the range of from 1 mm/Hg pressure up to 200 atmospheres pressure, absolute during the reaction, simultaneously removing water of reaction from the reaction mass, and then distilling the resulting product at a temperature in the range of from 51° up to 103° C. and a pressure in the range of from 0.7 up to 2.0 mm/Hg, with the proviso that when a potassium acid sulfate catalyst is used, the temperature of reaction is in the range of 180°–200° C.; and with the further proviso that when using a paratoluene sulfonic acid catalyst, the reaction temperature is in the range of from 115° C. up to 200° C. and (ii) the remainder of said composition being at least one food flavoring adjuvant selected from the group consisting of:
Natural orange oil;
Acetaldehyde;
Ethyl acetate;
Ethyl butyrate;
Propanal;
Maltol;
Ethyl maltol;
Ethyl propanal;
n-Decanal;
3-Hexenol;
n-Octanal;
n-Hexanal;
Citral;
Fusel oil;
n-Hexanal;
n-Butanol;
d-Limonene;
Linalool;
Citronellal
n-dodecanal;
Geraniol;
Nerol;
Vanillin;
trans-2-ethylidene-6-methyl-cis-B 3-heptenal;
trans-2-ethylidene-trans-3-hexenal;
cis-2-ethylidene-cis-3-hexenal;
cis-2-ethylidene-cis-3-hexenal diethylacetal; and
trans-2-ethylidene-cis-3-pentenal.

7. The food flavoring composition of claim 6 containing an addition a carrier.

* * * * *